United States Patent
Saliba et al.

(10) Patent No.: US 10,727,414 B2
(45) Date of Patent: Jul. 28, 2020

(54) FUNCTIONAL HOLE TRANSPORT MATERIALS FOR OPTOELECTRONIC AND/OR ELECTROCHEMICAL DEVICES

(71) Applicant: ECOLE POLYTECHNIQUE FEDERALE DE LAUSANNE (EPFL), Lausanne (CH)

(72) Inventors: Michael Saliba, Lausanne (CH); Mohammad Khaja Nazeeruddin, Ecublens (CH); Michael Graetzel, St-Sulpice (CH); Klaus-Hermann Dahmen, Marietta, GA (US); Gianluca Pozzi, Almenno San Salvatore (IT); Simonetta Orlandi, Milan (IT)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 40 days.

(21) Appl. No.: 15/738,279

(22) PCT Filed: Jun. 20, 2016

(86) PCT No.: PCT/IB2016/053657
§ 371 (c)(1),
(2) Date: Dec. 20, 2017

(87) PCT Pub. No.: WO2016/207775
PCT Pub. Date: Dec. 29, 2016

(65) Prior Publication Data
US 2018/0190911 A1 Jul. 5, 2018

(30) Foreign Application Priority Data

Jun. 25, 2015 (EP) ..................... 15173936

(51) Int. Cl.
*H01B 1/00* (2006.01)
*H01L 51/00* (2006.01)
(Continued)

(52) U.S. Cl.
CPC ........ *H01L 51/0061* (2013.01); *C07D 495/10* (2013.01); *C07D 495/22* (2013.01);
(Continued)

(58) Field of Classification Search
CPC . H01B 1/00; H01B 1/12; H01B 1/121; H01B 1/124; H01L 51/00; H01L 51/42;
(Continued)

(56) References Cited

FOREIGN PATENT DOCUMENTS

EP         2804232 A1    11/2014
WO    WO 2013/121835    *  8/2013

OTHER PUBLICATIONS

Hsiao-Fan Chen et al.; Spiro-configured bipolar hosts incorporating 4,5-diazafluroene as the electron transport moiety for highly efficient red and green phosphorescent OLEDs; Journal of Materials Chemistry; 2012; pp. 9658-9664; No. 22; Copyright The Royal Society of Chemistry 2012.
(Continued)

*Primary Examiner* — Mark Kopec
(74) *Attorney, Agent, or Firm* — Taft Stettinius & Hollister LLP

(57) ABSTRACT

The present invention relates to a compound of formula (I) based on a structure including functionalized spirofluorene and fused aromatics or non-aromatic rings with at least one heteroatom, and used as hole transporting material in a optoelectronic and/or photoelectrochemical device.

14 Claims, 5 Drawing Sheets

HT-SO7   Ar = Ph
HT-SO8   Ar = p-C₆H₁₃OC₆H₄
HT-SO9   Ar = p-MeC₆H₄
HT-SO10  Ar = p-PhOC₆H₄

(51) Int. Cl.
*H01L 51/42* (2006.01)
*C07D 495/10* (2006.01)
*H01B 1/12* (2006.01)
*C07D 495/22* (2006.01)
*H01G 9/20* (2006.01)
*H01L 51/50* (2006.01)

(52) U.S. Cl.
CPC ........... *H01B 1/121* (2013.01); *H01G 9/2059* (2013.01); *H01L 51/0032* (2013.01); *H01L 51/0074* (2013.01); *H01L 51/0077* (2013.01); *H01L 51/4226* (2013.01); *H01G 9/2031* (2013.01); *H01L 51/5004* (2013.01); *H01L 51/5056* (2013.01); *H01L 2251/552* (2013.01); *Y02E 10/549* (2013.01)

(58) Field of Classification Search
CPC ... C07C 211/00; C07C 211/33; C07C 211/57; C07C 211/61; C07D 495/10 C07D 495/22
See application file for complete search history.

(56) References Cited

OTHER PUBLICATIONS

Victorien Jeux et al.; Synthesis of Spiro[cyclopenta[1,2-b:5,4-b']DiThiophene-e,9'-Fluorenes] SDTF dissymmetrically functionalized; Tetrahedron Letters; 2015; pp. 1383-1387; No. 56; Copyright 2015 Elsevier Ltd.

Ullrich Mitschke et al.; Synthesis, characterization, and electrogenerated chemiluminescence of phenyl-substituted, phenyl-annulated, and spirofluorenyl-bridged oligothiophenes; J. Chem. Soc.; 2001; pp. 740-753; Perkin Translation 1; Copyright The Royal Society of Chemistry 2001.

Bo Xu et. al.; Carbazole-Based Hole-Transport Materials for Efficient Solid-State Dye-Sensitized Solar Cells and Perovskite Solar Cells; Advanced Materials; 2014; pp. 6629-6634; Copyright 2014 Wiley-VCH Verlag GmbH & Co. KGaA, Weinheim.

International Search Report; European Patent Office; International Application No. PCT/IB2016/053657; dated Sep. 23, 2016; 4 pages.

Written Opinion of the International Searching Authority; European Patent Office; International Application No. PCT/IB2016/053657; dated Sep. 23, 2016; 6 pages.

\* cited by examiner

FUNCTIONAL HOLE TRANSPORT MATERIALS FOR OPTOELECTRONIC AND/OR ELECTROCHEMICAL DEVICES

CROSS REFERENCE TO RELATED APPLICATIONS

This application is a U.S. national stage filing of International Patent Application No. PCT/IB2016/053657 filed on Jun. 20, 2016, which claims priority to European Application No. 15173936.4 filed on Jun. 25, 2015, the contents of each application hereby incorporated by reference in their entirety.

TECHNICAL FIELD

The present invention relates to organic compounds, their use as hole transport materials and their use to tune HOMO level, to optoelectronic and/or electrochemical devices, in particular solar cells and solid state solar cells comprising these compounds.

BACKGROUND ART AND PROBLEMS SOLVED BY THE INVENTION

The conversion of solar energy to electrical current using thin film third generation photovoltaics (PV) is being widely explored for the last two decades. The sandwich/monolithic-type PV devices, consisting of a mesoporous photoanode with an organic/inorganic light harvester, redox electrolyte/solid-state hole conductor, and counter electrode, have gained significant interest due to the ease of their fabrication, the flexibility in the selection of materials and the low cost effective production.

Recently, bulk layers of organometallic halide perovskite based on tin ($CsSnX_3$), or lead ($CH_3NH_3PbX_3$; X=Cl, Br, I) have been introduced pigment for light harvesting, resulting in high power conversion efficiencies (PCE). These perovskite materials show exceptional characteristics: large panchromatic absorption and very good charge-carrier mobility values being comparable to the amorphous silicon. Minimizing energy losses while favoring charge-extraction rates are fundamental to take advantage of the intrinsic properties of the perovskites and to improve the efficiency.

Therefore, perovskite-based and other types of solid state solar cells generally contain an organic hole transport material (HTM) layer, for transporting holes created by charge separation at the light harvester to the counter electrode and/or cathode for filling up by incoming electrons, thereby closing the electric circuit and rendering the devices regenerative. Currently most performing solid state device use doped Spiro-OMeTAD (2,2',7,7'-tetrakis(N,N-di-p-methoxyphenyl amine)-9,9-spirobifluorene) as a HTM. The relatively low PCE of solid state devices was often ascribed to the low hole mobility in Spiro-OMeTAD, which causes interfacial recombination losses by two orders of magnitude higher than in electrolyte-based, dye-sensitized solar cells (DSCCs). Further, the use of spiro-MeOTAD as hole transporting material may trigger instability in such solid-state solar cells. Because Spiro-MeOTAD has two oxidation potentials being very close, this HTM in the oxidized form is able to form a di-cation, which in turn can dismutate and might cause device instability. Further, since spiro-OMeTAD compound is present in semi-crystalline form, there is the risk that it will (re)crystallize in the processed form in the solar cell. In addition, the solubility in customary process solvents is relatively low, which leads to a correspondingly low degree of pore filling. Along stability issues, the high cost due to a complicated synthetic route and the high purity that is required (sublimation grade) in order to have good performance have been the main drawbacks for commercial applications of solid state solar cells.

Attempts were made to find an alternate organic HTM having higher charge carrier mobility and matching HOMO level to replace Spiro-OMeTAD. In most of the cases, it is difficult to compete with the performances equivalent to Spiro-OMeTAD-based devices, due to its unique properties: sufficient hole mobility, thermal and UV stability, and well-matched HOMO (highest occupied molecular orbital) energy level to the semiconductor light absorbers.

More recently a number of studies indicated that the HTMs can play a key role in controlling the long-term stability of perovskites solar cell. It was demonstrated that perovskites solar cell are more stable if the organic semiconductors are replaced by carbon as HTMs. Furthermore, it was shown that employing new dopant-free organic HTMs significantly improves the device stability compared to the commonly used chemical doped spiro-OMeTAD.

In view of the above, the present invention addresses the disadvantage of triggering instability and reducing life-time of the device comprising perovskite due to the presence of HTM, e.g. spiro-OMeTAD.

The present invention also pursues to provide new hole transporting material allowing to tune HOMO level and having positive impact on the sensitizer through its passivation to improve and provide higher power conversion efficiency (PCE) to photovoltaic devices comprising perovskite as well as to further optoelectronic devices Organic Light Emitting Diodes (OLED), Field effect Transistors (FET).

The present invention also addresses the disadvantage of the expensive and complex synthesis of HTMs resulting in materials of high price because of the expensive purification steps, starting material compounds, the complexity and the multiplication of reaction steps, the use of aggressive reagents. Thus the synthesis process is lengthy, time-consuming and expensive and causes non-negligible environmental impact.

The invention pursues to provide an efficient solar cell, which can be rapidly prepared in an efficient way, using readily available or low cost materials such as conductive material, using a short manufacturing procedure based on industrially known manufacturing step, keeping the material costs and the material impact on the environment very low.

The present invention addresses the problems depicted above.

SUMMARY OF THE INVENTION

Remarkably, in some aspects, the present inventors have found that a compound based on a structure comprising functionalized spirofluorene and fused aromatics or non-aromatic rings with at least one heteroatom contributes to both effective charge extraction (HTM function) and photocurrent enhancement (passivation of the perovskite layer, good electron transmission performance and cavity transmission performance) in a solid photovoltaic device and improves the PCE of optoelectronic and/or photoelectrochemical device, and in particular optoelectronic and/or photoelectrochemical device comprising perovskite pigment as sensitizer. They are non-planar efficient conjugate structure Although their large size, said compounds are good soluble in organic solvents, which greatly facilitates their purification and processing and their application or deposition on the sensitizer layer in the solid photovoltaic device.

The present invention provides a compound of formula (I)

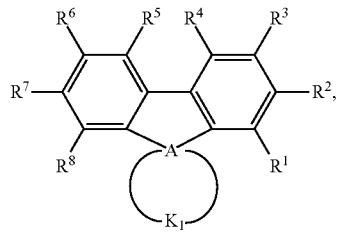

(I)

wherein A is selected from Si or C atom; wherein at least one substituent $R^1$, $R^2$, $R^3$, $R^4$, $R^5$, $R^6$, $R^7$ and $R^8$ is independently selected from substituents comprising 1-50 carbons, 1-20 heteroatoms being selected from O, S, N, and 0-2 P-hydrocarbyl, from halogen being selected from Cl, F, Br, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and P(=O)—, from and wherein alkyl, heteroalkyl, alkylaryl if they comprise 3 or more carbons, may be linear, branched or cyclic; and wherein any one of $R^1$, $R^2$, $R^3$, $R^4$, $R^5$, $R^6$, $R^7$ or $R^8$ being different from said substituents as defined above is H; and wherein $K_1$ is a conjugated system or a system of fused aromatics rings or fused non-aromatic rings comprising at least one heteroatom being selected from O, S and N, preferably from O, S, and N, wherein said aromatic rings may be further substituted by substituents being independently selected from H, and substituents as defined above for $R^1$, $R^2$, $R^3$, $R^4$, $R^5$, $R^6$, $R^7$ or $R^8$.

In an aspect, the present invention provides a compound of formula (I)

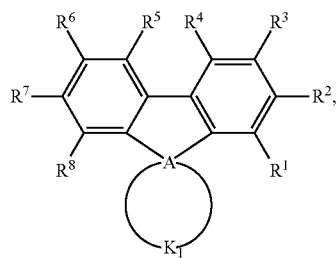

(I)

wherein

A is selected from Si or C atom;

$R^1$, $R^2$, $R^3$, $R^4$, $R^5$, $R^6$, $R^7$ and $R^8$ is independently selected from H, substituents comprising 1-50 carbons, 0-2 P-hydrocarbyl group, 1-20 heteroatoms being selected from 0, S, N, from halogen being selected from Cl, F, Br, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, from —C≡N, and wherein alkyl, heteroalkyl, alkylaryl if they comprise 3 or more carbons, may be linear, branched or cyclic;

at least one $R^1$, $R^2$, $R^3$, $R^4$, $R^5$, $R^6$, $R^7$ and $R^8$ is different from H;

at least one $R^1$, $R^2$, $R^3$, $R^4$, $R^5$, $R^6$, $R^7$ or $R^8$ being different from H atom is independently selected from a substituent of formula (1)

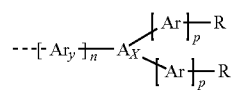

(1)

wherein n and p is an integer selected from 0, 1 or 2;

$A_X$ is selected from N or P(=O);

$Ar_y$ and Ar are independently selected from a monocyclic system or a polycyclic system comprising fused aromatic rings or conjugated monocyclic aromatic rings, said ring comprising 0, 1 or 2 heteroatoms being selected from O, S and N, and is further substituted in addition to R by other substituents independently selected from H, halogen, C1-C10 alkyl, C1-C10 alkoxy group, C1-C10 alkylthio (—S-alkyl) and —C≡N;

R is selected from H, $R_1$, —$NR_1R_2$, —O—$R_1$, —P(=O)$R_1R_2$, —S—$R_1$, or halogen, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl, wherein said alkyl, alkoxy, alkoxyalkyl, alkenyl and alkynyl, if they comprise 3 or more carbons, may be linear, branched or cyclic and wherein aryl, heteroaryl, alkyl, alkenyl, alkynyl may be further substituted by alkoxy group, alkylthio group and alkyl; and wherein any one of $R^1$, $R^2$, $R^3$, $R^4$, $R^5$, $R^6$, $R^7$ or $R^8$ being different from said substituents as defined above is H;

$K_1$ is a conjugated system or a system of fused aromatics rings or fused non-aromatic rings comprising at least one heteroatom being selected from O, S and N, preferably from O, S, and N, wherein said aromatic rings may be further substituted by substituents being independently selected from H, and substituents being different from H as defined above for $R^1$, $R^2$, $R^3$, $R^4$, $R^5$, $R^6$, $R^7$ or $R^8$.

In an embodiment, the compound of invention is selected from a compound of formula (Ia), (Ib) or (Ic).

In a further embodiment, the compound of the invention being a compound of formula (Ia) is selected from a compound of formula (Id), the compound of the invention being the compound of formula (Ib) is selected from a compound of formula (Ie) and the compound of the invention being the compound of formula (Ic) is selected from a compound of formula (If).

In a further aspect, the invention provides a hole transporting material comprising at least one compound selected from a compound according to any one of formulae (I), (Ia), (Ib), (Ic), (Id), (Ie) and (If).

In another aspect, the invention provides an optoelectronic and/or photoelectrochemical device comprising at least one compound selected from a compound according to any one of formulae (I), (Ia), (Ib), (Ic), (Id), (Ie) and (If)

In an embodiment, the optoelectronic and/or photoelectrochemical device of the invention is selected from an organic photovoltaic device, a photovoltaic solid state device, an p-n heterojunction, an organic solar cell, a dye sensitized solar cell, a solid state solar cell, a phototransistor, photodetector, particle detector and OLED (organic light-emitting diode).

In a particular embodiment, the optoelectronic and/or photoelectrochemical device of the invention is selected from a photovoltaic solid state device being a solid state solar cell comprising an organic-inorganic perovskite as sensitizer under the form of a layer.

In a further aspect, the invention provides use of a compound of the invention as a tuner of HOMO level.

Further aspects and preferred embodiments of the invention are detailed herein below and in the appended claims. Further features and advantages of the invention will become apparent to the skilled person from the description of the preferred embodiments given below.

DETAILED DESCRIPTION OF THE PREFERRED EMBODIMENTS

Figure 1A:
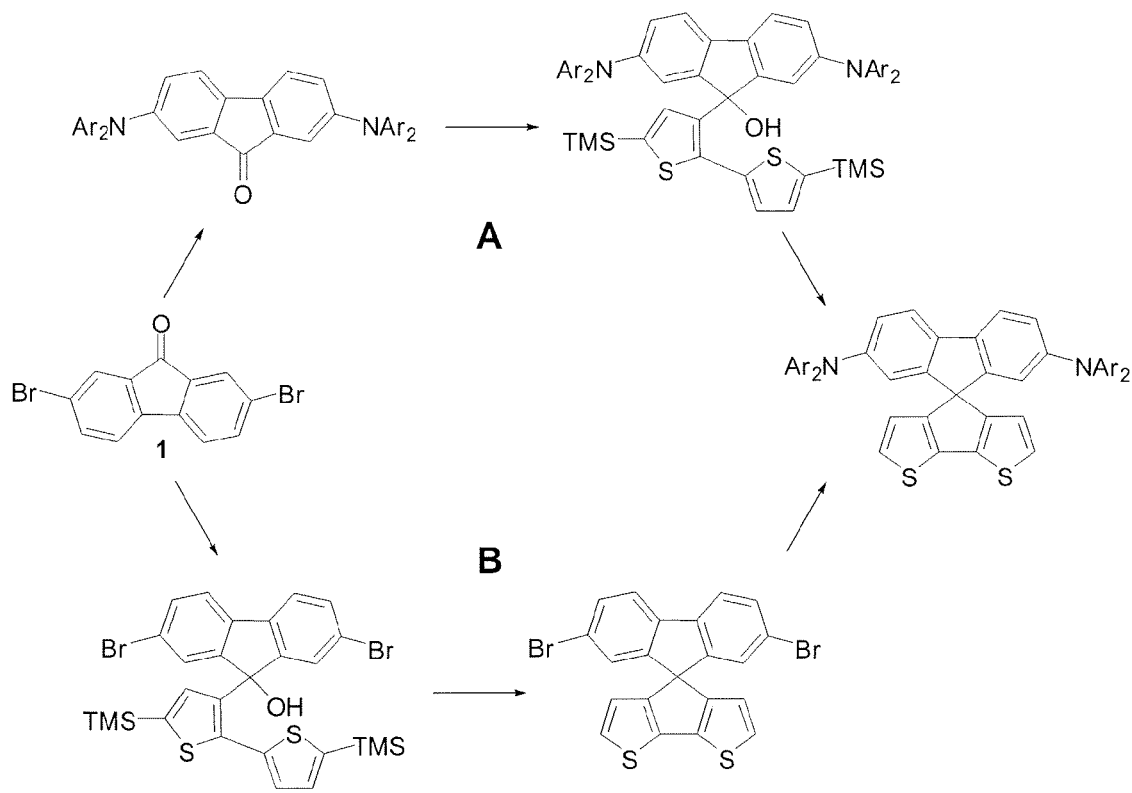
FIG. 1A shows scheme of two strategies A and B for the synthesis of the compound of the invention HT-SO2.

The present invention concerns a compound of formula (I) based on a structure comprising spiro diarylamino functionalized fluorene and fused aromatics rings with at least one heteroatom contributes.

In particular, the invention concerns a compound of formula (I)

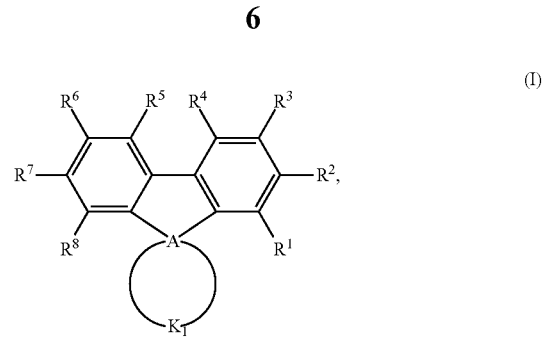

wherein
A is selected from Si or C atom;
at least one $R^1$, $R^2$, $R^3$, $R^4$, $R^5$, $R^6$, $R^7$ and $R^8$ is independently selected from substituents comprising 1-50 carbons, 1-20 heteroatoms being selected from O, S, N, and 0-2 P-hydrocarbyl, from halogen being selected from Cl, F, Br, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, —C≡N, and wherein alkyl, heteroalkyl, alkylaryl if they comprise 3 or more carbons, may be linear, branched or cyclic; and wherein any one of $R^1$, $R^2$, $R^3$, $R^4$, $R^5$, $R^6$, $R^7$ or $R^8$ being different from said substituents as defined above is H; and
$K_1$ is a conjugated system or a system of fused aromatics rings or fused non-aromatic rings comprising at least one heteroatom being selected from O, S and N, preferably from 0, S, and N, wherein said aromatic rings may be further substituted by substituents being independently selected from H, and substituents as defined above for $R^1$, $R^2$, $R^3$, $R^4$, $R^5$, $R^6$, $R^7$ or $R^8$.

More particularly, the present invention provides a compound of formula (I)

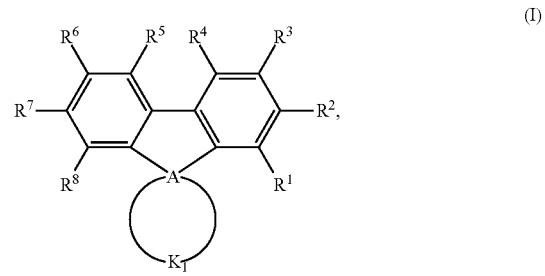

wherein
A is selected from Si or C atom;
$R^1$, $R^2$, $R^3$, $R^4$, $R^5$, $R^6$, $R^7$ and $R^8$ is independently selected from H, substituents comprising 1-50 carbons, 0-2 P-hydrocarbyl group, 1-20 heteroatoms being selected from O, S, N, from halogen being selected from Cl, F, Br, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, from —C≡N, and wherein alkyl, heteroalkyl, alkylaryl if they comprise 3 or more carbons, may be linear, branched or cyclic;

at least one $R^1$, $R^2$, $R^3$, $R^4$, $R^5$, $R^6$, $R^7$ and $R^8$ is different from H;

at least one $R^1$, $R^2$, $R^3$, $R^4$, $R^5$, $R^6$, $R^7$ or $R^8$ being different from H atom is independently selected from a substituent of formula (1)

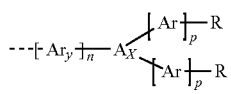 (1)

wherein n and p is an integer selected from 0, 1 or 2;

$A_X$ is selected from N or P(=O);

$Ar_y$ and Ar are independently selected from a monocyclic system or a polycyclic system comprising fused aromatic rings or conjugated monocyclic aromatic rings, said ring comprising 0, 1 or 2 heteroatoms being selected from O, S and N, and is further substituted in addition to R by other substituents independently selected from H, halogen, C1-C10 alkyl, C1-C10 alkoxy group, C1-C10 alkylthio (—S-alkyl) and —C≡N;

R is selected from H, $R_1$, —$NR_1R_2$, —O—$R_1$, —P(=O)$R_1R_2$, —S—$R_1$, or halogen, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl, wherein said alkyl, alkoxy, alkoxyalkyl, alkenyl and alkynyl, if they comprise 3 or more carbons, may be linear, branched or cyclic and wherein aryl, heteroaryl, alkyl, alkenyl, alkynyl may be further substituted by alkoxy group, alkylthio group and alkyl; and wherein any one of $R^1$, $R^2$, $R^3$, $R^4$, $R^5$, $R^6$, $R^7$ or $R^8$ being different from said substituents as defined above is H;

$K_1$ is a conjugated system or a system of fused aromatics rings or fused non-aromatic rings comprising at least one heteroatom being selected from O, S and N, preferably from O, S, and N, wherein said aromatic rings may be further substituted by substituents being independently selected from H, and substituents being different from H as defined above for $R^1$, $R^2$, $R^3$, $R^4$, $R^5$, $R^6$, $R^7$ or $R^8$.

A is an integral part from the conjugated system or the system of fused aromatic or non-aromatic rings. Preferably A is C atom.

Said fused aromatic rings may be derived from two fused C4-C7 or C4-C6 hetero-aromatic or non-aromatic hetero-rings.

In a further embodiment, K1 is a conjugated system or a system of fused aromatics rings or fused non-aromatic rings comprising at least one heteroatom being selected from O, S and N, preferably from O, S, and N, more preferably from N and S, wherein said aromatic rings may be substituted by substituent being independently selected from H, substituents comprising 1-50 carbons, 1-20 heteroatoms being selected from O, S, N, and 0-2 P-hydrocarbyl, from halogen being selected from Cl, F, Br, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, from —C≡N, and wherein alkyl, heteroalkyl, alkylaryl if they comprise 3 or more carbons, may be linear, branched or cyclic.

$K_1$ may be a conjugated system or a system of fused aromatics rings or fused non-aromatic rings comprising at least one heteroatom being selected from O, S and N, preferably from 0, S, and N, more preferably from N and S, wherein said aromatic rings may be substituted by H, halogen being selected from Cl, F, Br, by C1-C30 alkyl or C1-C30 heteroalkyl, wherein the heteroatom is selected from O, S, Se, N and —P(=O)—, by —C≡N, by C4-C20 aryl, C4-C20 heteroaryl group, C4-C30 alkylaryl group, C4-C30 aryloxy group or C4-C20 heteroaryloxy group, wherein alkyl, heteroalkyl, alkylaryl if they comprise 3 or more carbons, may be linear, branched or cyclic In another embodiment, said at least one $R^1$, $R^2$, $R^3$, $R^4$, $R^5$, $R^6$, $R^7$ and $R^8$ is independently selected from substituents comprising 1-50 carbons, 1-20 heteroatoms being selected from O, S, N, and 0-2 P-hydrocarbyl, said substituents being further substituted by substituents selected from H, halogen, C1-C10 alkyl, C1-C10 alkoxy group, C1-C10 alkylthio (—S-alkyl) and —C≡N and wherein any one of $R^1$, $R^2$, $R^3$, $R^4$, $R^5$, $R^6$, $R^7$ or $R^8$ being different from said substituents comprising 1-50 carbons, 1-20 heteroatoms and 0-2 P-hydrocarbyl is H.

Preferably $K_1$ is selected from a system comprising fused aromatic rings or fused non-aromatic rings comprising at least one heteroatom being selected from O, S and N, preferably from O, S, and N, more preferably from N and S, wherein said aromatic rings may be substituted by substituent being independently selected from H, substituents comprising 1-50 carbons, 1-20 heteroatoms being selected from O, S, N, and 0-2 P-hydrocarbyl, from halogen being selected from Cl, F, Br, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, from —C≡N, and wherein alkyl, heteroalkyl, alkylaryl if they comprise 3 or more carbons, may be linear, branched or cyclic.

In another embodiment, $K_1$ is a conjugated system or a system of fused aromatics rings or fused non-aromatic rings comprising at least one heteroatom being selected from O, S and N, preferably from O, S, and N, more preferably from N and S, wherein said aromatic rings may be substituted by H, halogen being selected from Cl, F, Br, by C1-C30 alkyl or C1-C30 heteroalkyl, wherein the heteroatom is selected from O, S, Se, N and —P(=O)—, by —C≡N, by C4-C20 aryl, C4-C20 heteroaryl group, C4-C30 alkylaryl group, C4-C30 aryloxy group or C4-C20 heteroaryloxy group, wherein alkyl, heteroalkyl, alkylaryl if they comprise 3 or more carbons, may be linear, branched or cyclic, and by 0, 1 or 2 substituents selected from an amino group, P-hydrocaryl or a mono- or polycyclic system comprising fused aromatic rings or monocyclic aromatic rings bound together by covalent bond, said ring comprising 0, 1 or 2 heteroatoms being selected from O, S and N, and wherein said amino group, said P-hydrocarbyl and said mono- or polycyclic group may further substituted by H, halogen, $R_1$, —$NR_1R_2$, —O—$R_1$, —P(=O)$R_1R_2$, or —S—$R_1$, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl wherein said alkyl, alkoxy, alkoxyalkyl, alkenyl and alkynyl, if they comprise 3 or more carbons, may be linear, branched or cyclic or optionally fluorinated.

In a further embodiment, $K_1$ is a conjugated system or a system of fused aromatics rings or fused non-aromatic rings comprising at least one heteroatom being selected from O, S and N, preferably from O, S, and N, more preferably from N and S, wherein said aromatic rings may be substituted by H.

In an embodiment, the compound of formula (I) is selected from a compound of formula (Ia), (Ib) or (Ic)

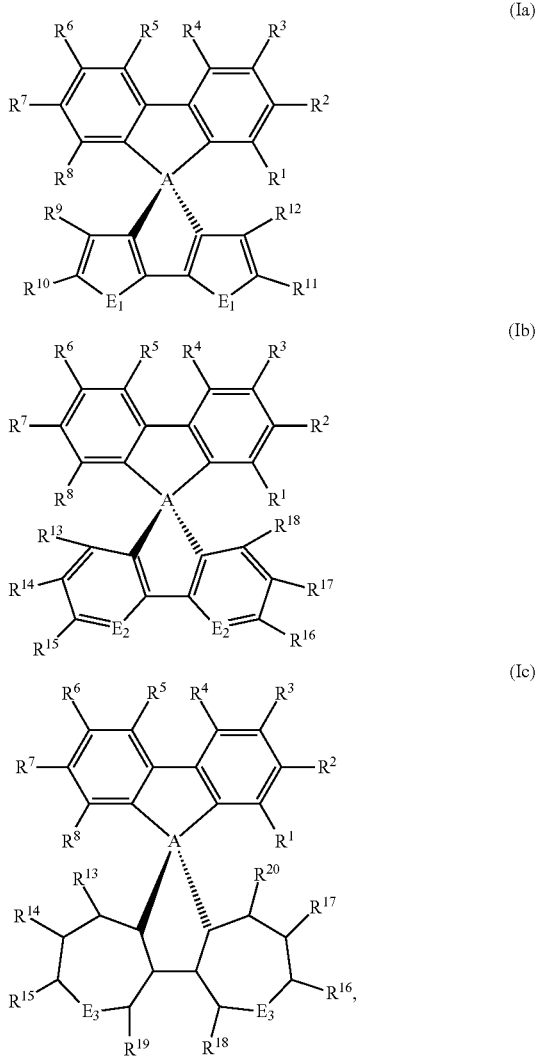

wherein
$E_1$ is selected from O, S and N, $E_2$ is selected from $OR^2$ or $SR^{22}$, $R^{22}$ being selected from $BF_4^-$, $PF_6^-$, $CF_3SO_3^-$ and halogen$^-$ being selected from $Cl^-$, $F^-$, $Br^-$, or $I^-$, $E_3$ is selected from O, S, $NR^{21}$ or N according to the valence, wherein $R^{21}$ is independently selected from H, halogen being selected from Cl, F, Br, or I, from C1-C30 alkyl, C1-C30 heteroalkyl, C4-C30 aryl and C4-C30 heteroaryl, the heteroatom being selected from O, S, and N;
$R^1$, $R^2$, $R^3$, $R^4$, $R^5$, $R^6$, $R^7$ or $R^8$ are independently selected from substituent as defined above; and
$R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are independently selected from H, halogen being selected from Cl, F, Br, or I, from —C≡N, C1-C30 alkyl, C1-C30 heteroalkyl, C4-C20 aryl, C4-C20 heteroaryl, C4-C30 alkylaryl group, C4-C30 aryloxy group or C4-C20 heteroaryloxy group wherein the heteroatom is selected from O, S, N and —P(=O)—, preferably from O, S, and N, more preferably from O and S, wherein alkyl, heteroalkyl, alkylaryl if they comprise 3 or more carbons, may be linear, branched or cyclic, and from a substituent being different from H as defined above for $R^1$, $R^2$, $R^3$, $R^4$, $R^5$, $R^6$, $R^7$ or $R^8$.

In a further embodiment, $E_1$ is selected from O, S and N, preferably from O and S, $E_2$ is selected from $OR^{22}$ or $SR^{22}$, $R^{22}$ being selected from $BF_4^-$, $PF_6^-$, $CF_3SO_3^-$ and halogen$^-$ being selected from $Cl^-$, $F^-$, $Br^-$, or $I^-$, $E_3$ is selected from $NR^{21}$ or N in respect with valence, preferably $NR^{21}$, wherein $R^{21}$ is independently selected from H, halogen being selected from Cl, F, Br, or I, from C1-C12 alkyl, C1-C12 heteroalkyl, C4-C12 aryl and C4-C12 heteroaryl, the heteroatom being selected from O, S, and N.

The fused C6 heterorings of the compound of formula (Ic) are not aromatic. Formula (Ic) represents one form of said fused C6 heterorings. Formula (Ic) is not limited to the above-represented structure of the fused C6 non-aromatic heterorings and may encompass the following structures:

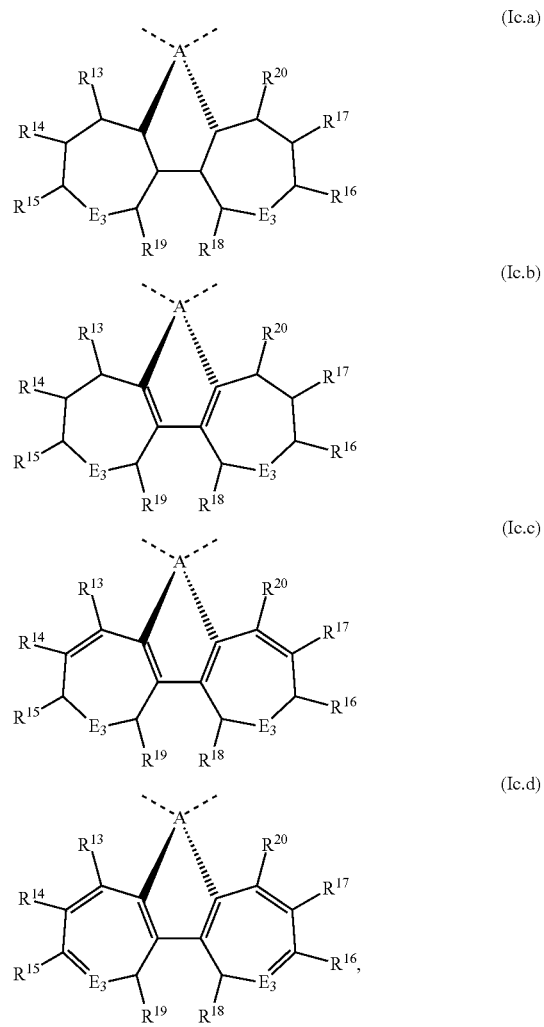

wherein the dotted lines represent the bond to the spiro-fluorene moiety, $E_3$ and $R^{13}$, $R^{14}$, $R^{15}$, $R^{16}$, $R^{17}$, $R^{18}$, $R^{19}$ and $R^{20}$ are defined as above and $E_3$ of the structure (Ic.c) is N according to the valence. In particular the fused non-aromatic C6 heterorings in the formula (Ic) encompasses any one of formulae (Ic.a), (Ic.b) and (Ic.c), preferably (Ic.a).

Preferably $R^{21}$ is H.

All $E_1$ moieties in the compound of formula (Ia) may be different or identical, preferably identical. All $E_2$ moieties in the compound of formula (Ib) may be different or identical, preferably identical.

$R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ of the compounds of formula (Ia), (Ib) and/or formula (Ic) may be substituted by substituents independently selected from H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, if they comprise 3 or more carbons, may be linear, branched or cyclic, wherein halogen is selected from Cl, F, Br, or I.

Preferably cyanoalkyl, alkyl, alkoxy, alkoxyalkyl, haloalkyl, haloalkoxyalkyl being substituents of $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ of the compounds of formula (Ia), (Ib) and/or formula (Ic) are selected from hydrocarbon, hydrocarbyl, heterocarbon or heterocarbyl containing from 1 to 16 carbons, 1 to 12 carbons, 1 to 9 carbons, 1 to 6 carbons and may contain 0-10 heteroatom and 0-1 halogen being selected from Cl, F, Br or I, and, if they comprise 3 or more carbons, they may be linear, branched or cyclic, preferably linear or branched.

In other embodiment, at least one $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are independently selected from a substituent as defined for $R^1$, $R^2$, $R^3$, $R^4$, $R^5$, $R^6$, $R^7$ or $R^8$.

In another embodiment, at least one $R^9$, $R^{10}$, $R^{11}$, $R^{12}$, $R^{13}$, $R^{14}$, $R^{15}$, $R^{16}$, $R^{17}$, $R^{18}$, $R^9$ and $R^{20}$ is selected from an amino group, P-hydrocarbyl or a mono- or polycyclic system comprising fused aromatic rings or monocyclic aromatic rings bound together by covalent bond, said ring comprising 0, 1 or 2 heteroatoms being selected from O, S and N, and wherein said amino group, said P-hydrocarbyl and said mono- or polycyclic group may further substituted by H, halogen, $R_1$, —$NR_1R_2$, —O—$R_1$, —P(=O)$R_1R_2$, or —S—$R_1$, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl wherein said alkyl, alkoxy, alkoxyalkyl, alkenyl and alkynyl, if they comprise 3 or more carbons, may be linear, branched or cyclic.

In an embodiment the at least one $R^1$, $R^2$, $R^3$, $R^4$, $R^5$, $R^6$, $R^7$ and $R^8$ of the compound of the invention being different from H is independently selected from an amino group, P-hydrocaryl or a mono- or polycyclic system comprising fused aromatic rings or monocyclic aromatic rings bound together by covalent bond, said ring comprising 0, 1 or 2 heteroatoms being selected from O, S and N, and wherein said amino group, said P-hydrocarbyl and said mono- or polycyclic group may further substituted by H, halogen, $R_1$, —$NR_1R_2$, —O—$R_1$, —P(=O)$R_1R_2$, or —S—$R_1$, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl wherein said alkyl, alkoxy, alkoxyalkyl, alkenyl and alkynyl, if they comprise 3 or more carbons, may be linear, branched or cyclic.

In a further embodiment, according to the invention, the at least one $R^1$, $R^2$, $R^3$, $R^4$, $R^5$, $R^6$, $R^7$ or $R^8$ of the compounds of the invention, the compounds according to any one of formulae (I), (Ia), (Ib) and (Ic) being different from H atom is independently selected from a substituent of formula (1)

(1)

wherein n and p is an integer selected from 0, 1 or 2;

$A_X$ is selected from N or P(=O), preferably from N;

$Ar_y$ and Ar are independently selected from a monocyclic system or a polycyclic system comprising fused aromatic rings or conjugated monocyclic aromatic rings, said ring comprising 0, 1 or 2 heteroatoms being selected from O, S and N, and is further substituted in addition to R by other substituents independently selected from H, halogen, C1-C10 alkyl, C1-C10 alkoxy group, C1-C10 alkylthio (—S-alkyl) and —C≡N;

R is selected from H, $R_1$, —$NR_1R_2$, —O—$R_1$, —P(=O)$R_1R_2$, —S—$R_1$, or halogen, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl, wherein said alkyl, alkoxy, alkoxyalkyl, alkenyl and alkynyl, if they comprise 3 or more carbons, may be linear, branched or cyclic and wherein aryl, heteroaryl, alkyl, alkenyl, alkynyl may be further substituted by alkoxy group, alkylthio group and alkyl.

The dotted line in formula (1) represents the bond by which $Ar_y$, if $Ar_y$ present and n is 1 or 2, or $A_X$, if $Ar_y$ is absent, is connected to the aromatic ring of the fused ring system.

Preferably n is 0 or 1 p is 1 or 2. If $A_X$ is N, preferably n is 0 or 1 and p is 1 or 2. If $A_X$ is P(=O), preferably n is 1 and p is 1 or 2.

$Ar_y$ ($Ar_{y1}$ and $Ar_{y2}$) and Ar moieties ($Ar_1$ and $Ar_2$) may be identical or different. If $A_X$ is N, preferably n is 0 or 1, p is 1 or 2, and $Ar_{y1}$ (if present), $Ar_1$ and $Ar_2$ (if present) are identical. If $A_X$ is P(=O), preferably n is 1, p is 1 or 2, $Ar_{y1}$, $Ar_1$ and $Ar_2$ (if present) are identical or different, preferably identical.

In one embodiment, $A_X$ is N.

In an embodiment, $Ar_y$ and Ar of formula (1) are independently selected from moieties according to any one of formulae (2) to (19)

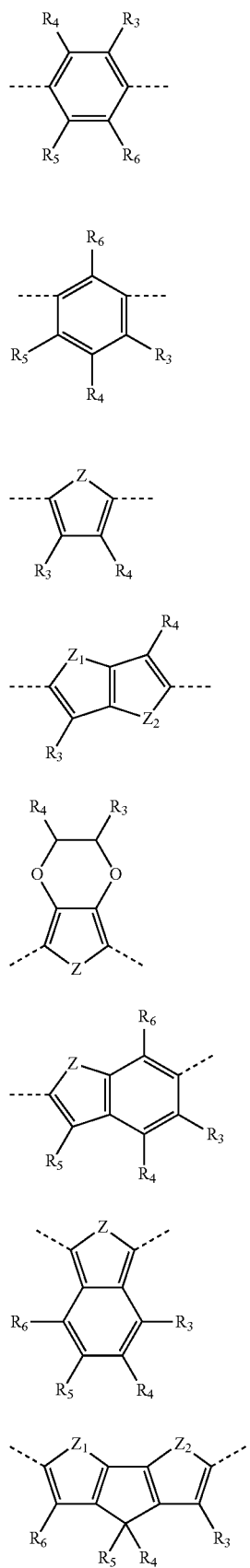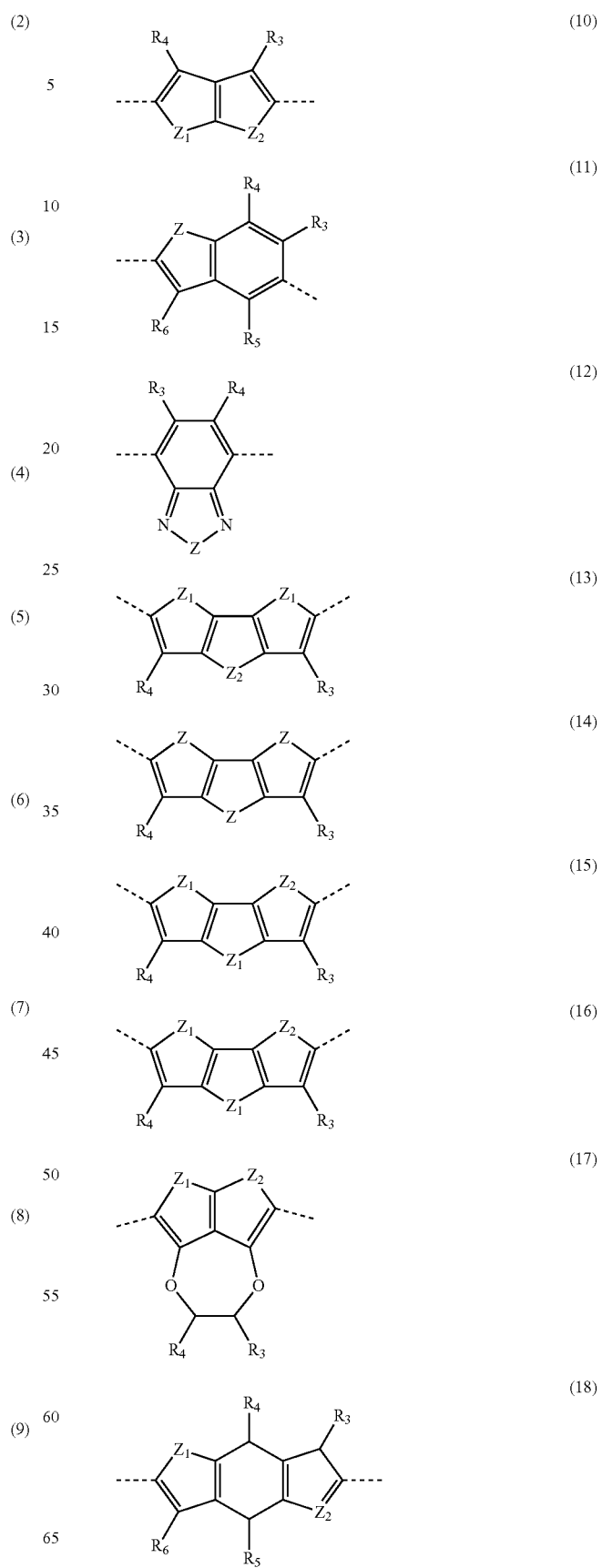

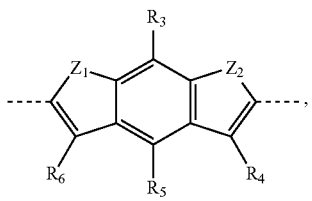

(19)

wherein

Z, $Z_1$, $Z_2$ are independently selected from O, S and Se atoms, $R_3$, $R_4$, $R_5$ and $R_6$ are independently selected from H, halogen, C1-C10 alkyl, C1-C10 alkoxy group, C1-C10 alkylthio (—S-alkyl) and —C≡N.

The dotted lines represent the bond by which, the substituents are connected to the aromatic ring of the fused ring system and/or to another substituents and/or to the N atom and/or to the P(=O).

Preferably Z, $Z_1$, $Z_2$ are independently selected from O and S.

In another embodiment, and Z, $Z_1$ and $Z_2$ are different from each other when they are present in the same moiety. In particular $Z_1$ and $Z_2$ are different from each other when they are present in the same moiety.

Preferably, $Ar_y$ and Ar are independently selected from moieties according to any one of formulae (2), (3), (4), (6), (13) and (14), more preferably from moieties according to any one of formulae (2), (3), and (4), preferably (2) and (3), in particular when n is 1 and p is 2.

One or more $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are selected from a substituent as defined above for $R^1$, $R^2$, $R^3$, $R^4$, $R^5$, $R^6$, $R^7$ or $R^8$ being different from H (atom). One, two, three or four, preferably two $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are selected from a substituent as defined above for $R^1$, $R^2$, $R^3$, $R^4$, $R^5$, $R^6$, $R^7$ or $R^8$ being different from H (atom). Preferably $R^{10}$ and $R^{11}$, $R^{15}$ and $R^{16}$, or $R^{14}$ and $R^{17}$ are selected from a substituent as defined above for $R^1$, $R^2$, $R^3$, $R^4$, $R^5$, $R^6$, $R^7$ or $R^8$ being different from H (atom).

In another embodiment $R^9$, $R^{11}$, $R^{12}$, $R^{13}$, $R^{14}$, $R^{15}$, $R^{16}$, $R^{17}$, $R^{18}$, $R^{19}$ and $R^{20}$ are independently selected from H, halogen being selected from Cl, F, Br, or I, C1-C30 alkyl, C1-C30 heteroalkyl, C4-C20 aryl, C4-C20 heteroaryl, C4-C30 alkylaryl group, C4-C30 aryloxy group or C4-C20 heteroaryloxy group wherein the heteroatom is selected from O, S, N and —P(=O)—, —C≡N, preferably from O, S, and N, more preferably from O and S, wherein alkyl, heteroalkyl, alkylaryl if they comprise 3 or more carbons, may be linear, branched or cyclic, and from a substituent of formula (1) as defined above.

In a further embodiment, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are independently selected from H and from a substituent of formula (1) as defined above. In particular at least one $R^9$, $R^{10}$, $R^{11}$, $R^{12}$, $R^{13}$, $R^{14}$, $R^{15}$, $R^{16}$, $R^{17}$, $R^8$, $R^{19}$ and $R^{20}$ is independently selected from a substituent of formula (1) as defined above. Preferably $R^{10}$ and $R^{11}$, $R^9$ and $R^{12}$, $R^{15}$ and $R^{16}$, or $R^{14}$ and $R^{17}$ are selected from a substituent of formula (1).

In an embodiment, $R^{10}$ and $R^{11}$ of compound of formula (Ia), and/or $R^9$ and $R^{12}$ of compound of formula (Ia), and/or $R^{15}$ and $R^{16}$ of a compound according to formula (Ib) or (Ic), or $R^{14}$ and $R^{17}$ of a compound according to formula (Ib) or (Ic) are selected from a substituent of formula (1). Preferably $R^{10}$ and $R^{11}$ of compound of formula (Ia), and/or $R^9$ and $R^{12}$ of compound of formula (Ia), and/or $R^{15}$ and $R^{16}$ of a compound according to formula (Ib) or (Ic), or $R^{14}$ and $R^{17}$ of a compound according to formula (Ib) or (Ic) are selected from a substituent of formula (1), the substituents $R^9$, $R^{10}$, $R^{11}$, $R^{12}$, $R^{13}$, $R^{14}$, $R^{15}$, $R^{16}$, $R^{17}$, $R^{18}$, $R^{19}$ or $R^{20}$, if different from a substituent of formula (1), are H.

Preferably $R^2$ and $R^7$ are selected from a substituent of formula (1) as defined above.

The compound of the invention of formula (I) may be selected from a compound of formula (Id), (Ie) or (If) below:

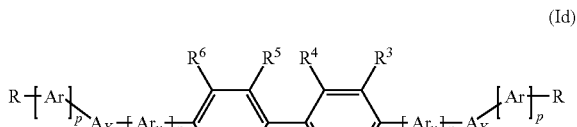

(Id)

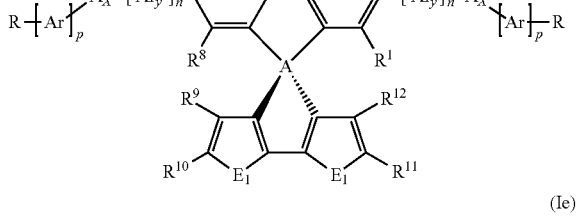

(Ie)

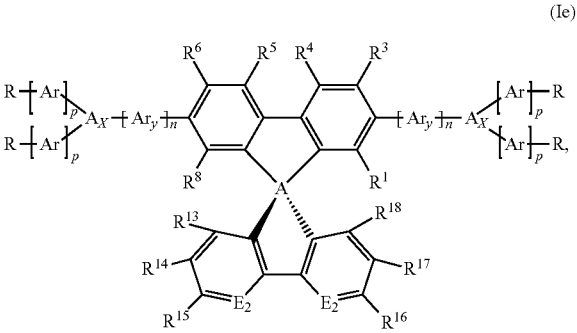

(If)

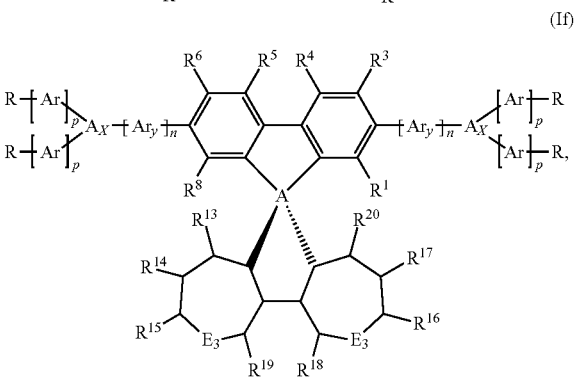

wherein A, $Ar_y$, $A_X$, Ar, n, p, R, $E_1$, $E_2$, $E_3$, $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are defined as above.

In an embodiment, the compound of the invention according to formula (Ia) is selected from a compound of formula (Id), the compound according formula (Ib) is selected from a compound of formula (Ie) and the compound according to formula (Ic) is selected from a compound of formula (If).

In an embodiment, $R^1$, $R^3$, $R^4$, $R^5$, $R^6$ and $R^8$ of the compound of the invention according to any one of formulae (I), (Ia), (Ib), (Ic), (Id), (Ie) and (If) are H.

$R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ of a compound according to any one of formulae (Ia), (Ib), (Ic), (Id), (Ie) and (If) are H. In particular, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ of a compound selected from a compound according to any one of formulae (Id), (Ie) and (If) are H.

In another embodiment $R^9$, $R^{12}$, $R^{13}$, $R^{14}$, $R^{15}$, $R^{16}$, $R^{17}$, $R^{18}$, $R^{19}$ and $R^{20}$ of a compound according to any one of formulae (Ia), (Ib), (Ic), (Id), (Ie) and (If) are H. Further $R^{13}$, $R^{18}$, $R^{19}$ and $R^{20}$ of a compound according to any one of formulae (Ia), (Ib), (Ic), (Id), (Ie) and (If) are H, and $R^9$ and $R^{12}$ are H if $R^{10}$ and $R^{11}$ are different from H, $R^{10}$ and $R^{11}$ are H if $R^9$ and $R^{12}$ are different from H, $R^{15}$ and $R^{16}$ are H if $R^{14}$ and $R^{17}$ are different from H, or $R^{14}$ and $R^{17}$ are H if $R^{15}$ and $R^{16}$ are different from H.

In an embodiment, $R^1$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ of a compound according to any one of formulae (Ia), (Ib), (Ic), (Id), (Ie) and (If) are H. In particular, $R^1$, $R^3$, $R^4$, $R^5$, $R^6$, $R^8$, $R^9$, $R^{12}$, $R^{13}$, $R^{15}$, $R^{16}$, $R^{18}$, $R^{19}$ and $R^{20}$ of a compound according to any one of formulae (Ia), (Ib), (Ic), (Id), (Ie) and (Ie) are H or $R^1$, $R^3$, $R^4$, $R^5$, $R^6$, $R^8$, $R^9$, $R^{12}$, $R^{13}$, $R^{14}$, $R^{17}$, $R^{18}$, $R^{19}$ and $R^{20}$ of a compound according to any one of formulae (Ia), (Ib), (Ic), (Id), (Ie) and (Ie) are H or $R^1$, $R^3$, $R^4$, $R^5$, $R^6$, $R^8$, $R^9$, $R^{12}$, $R^{13}$, $R^{15}$, $R^{16}$, $R^{18}$, $R^{19}$ and $R^{20}$ of a compound according to any one of formulae (Ia), (Ib), (Ic), (Id), (Ie) and (Ie) are H or $R^1$, $R^3$, $R^4$, $R^5$, $R^6$, $R^8$, $R^{10}$, $R^{11}$, $R^{13}$, $R^{14}$, $R^{17}$, $R^{18}$, $R^{19}$ and $R^{20}$ of a compound according to any one of formulae (Ia), (Ib), (Ic), (Id), (Ie) and (Ie) are H or $R^1$, $R^3$, $R^4$, $R^5$, $R^6$, $R^8$, $R^{10}$, $R^{11}$, $R^{13}$, $R^{15}$, $R^{16}$, $R^{18}$, $R^{19}$ and $R^{20}$ of a compound according to any one of formulae (Ia), (Ib), (Ic), (Id), (Ie) and (Ie) are H.

Preferably $R^9$, $R^{12}$, $R^{13}$, $R^{15}$, $R^{16}$, $R^{18}$, $R^{19}$ and $R^{20}$ of the compounds according to any one of formulae (Ia), (Ib), (Ic), (Id), (Ie) and (If) are H; $R^{10}$, $R^{11}$, $R^{14}$ and $R^{17}$ are selected from substituent as defined above but different from H. In particular, $R^{10}$, $R^{11}$, $R^{14}$ and $R^{17}$ are selected from substituent of formula (1) as defined above. In more particular, $R^{10}$ and $R^{11}$ are selected from substituent as defined above but different from H, and $R^{14}$ and $R^{17}$ are selected from substituent of formula (1) as defined above.

According to another preferred embodiment, $R^9$, $R^{12}$, $R^{13}$, $R^{14}$, $R^{17}$, $R^{18}$, $R^{19}$ and $R^{20}$ of the compounds according to any one of formulae (Ia), (Ib), (Ic), (Id), (Ie) and (If) are H; $R^{10}$, $R^{11}$, $R^{15}$ and $R^{16}$ are selected from substituent as defined above but different from H. In particular, $R^{10}$, $R^{11}$, $R^{15}$ and $R^{16}$ are selected from substituent of formula (1) as defined above. In more particular, $R^{10}$ and $R^{11}$ are selected from substituent as defined above but different from H, and $R^{15}$ and $R^{16}$ are selected from substituent of formula (1) as defined above.

In a further embodiment, $R^1$, $R^3$, $R^4$, $R^5$, $R^6$, $R^8$ and $R^9$, $R^{12}$, $R^{13}$, $R^{15}$, $R^{16}$, $R^{18}$, $R^{19}$, $R^{20}$ of a compound according to any one of formulae (Ia), (Ib), (Ic), (Id), (Ie) and (If) are H; $R^{10}$, $R^{11}$, $R^{14}$ and $R^{17}$ are selected from a substituent of formula (1) as defined above. Or, $R^1$, $R^3$, $R^4$, $R^5$, $R^6$, $R^8$ and $R^9$, $R^{12}$, $R^{13}$, $R^{14}$, $R^{17}$, $R^{18}$, $R^{19}$, $R^{20}$ of a compound according to any one of formulae (Ia), (Ib), (Ic), (Id), (Ie) and (If) are H; $R^{10}$, $R^{11}$, $R^{15}$ and $R^{16}$ are selected from a substituent of formula (1) as defined above In a further embodiment $R^1$, $R^3$, $R^4$, $R^5$, $R^6$, $R^8$ and $R^9$, $R^{12}$, $R^{13}$, $R^{15}$, $R^{16}$, $R^{18}$, $R^{19}$, $R^{20}$ of a compound according to any one of formulae (Ia), (Ib), (Ic), (Id), (Ie) and (If) are H; $R^2$, $R^7$ and $R^{10}$, $R^{11}$, $R^{14}$ and $R^{17}$ are selected from a substituent of formula (1) as defined above. Or, $R^1$, $R^3$, $R^4$, $R^5$, $R^6$, $R^8$ and $R^9$, $R^{12}$, $R^{13}$, $R^{14}$, $R^{17}$, $R^{18}$, $R^{19}$, $R^{20}$ of a compound according to any one of formulae (Ia), (Ib), (Ic), (Id), (Ie) and (If) are H; $R^2$, $R^7$ and $R^{10}$, $R^{11}$, $R^{15}$ and $R^{16}$ are selected from a substituent of formula (1) as defined above.

The compound of the invention is in particular used as hole transporting material and may function as a hole transporting material and as a hole injection material to bring holes extracted from a sensitizer to the hole collector of the photovoltaic device, e.g. a solid solar cell. This compound is able to passivate the sensitizer or the sensitizer layer and to improve the performance and the efficiency of such a device, and in particular an optoelectronic and/or photoelectrochemical device comprising an organic-inorganic perovskite as sensitizer.

By "hole transport material", "hole transporting material", "charge transporting material", "organic hole transport material" and "inorganic hole transport material", and the like, is meant any material or composition wherein charges are transported by electron or hole movement (electronic motion) across said material or composition. The "hole transport material" is thus an electrically conductive material. Such hole transport materials, etc., are different from electrolytes. In this latter, charges are transported by diffusion of molecules.

In an aspect, the invention provides a hole transporting material comprising at least one compound selected from formulae (I), (Ia), (Ib), (Ic), (Id), (Ie) and (If) as defined above.

The invention also provides an optoelectronic and/or photoelectrochemical device comprising at least one compound selected from a compound according to any one of formulae (I), (Ia), (Ib), (Ic), (Id), (Ie) and (If) as defined above.

The optoelectronic and/or photoelectrochemical device of the invention further comprises a hole transporting layer comprising said at least one compound of the invention selected from a compound according to any one of formulae (I), (Ia), (Ib), (Ic), (Id), (Ie) and (If) as defined above.

In another embodiment the optoelectronic and/or photoelectrochemical device of the invention is selected from an organic photovoltaic device, a photovoltaic solid state device, a p-n heterojunction, an organic solar cell, a dye sensitized solar cell, a solid state solar cell, a phototransistor, photodetector, particle detector and OLED (organic light-emitting diode). In particular the optoelectronic and/or photoelectrochemical device of the invention is a solar cell, a solid state solar cell or a photovoltaic solid state device.

The optoelectronic and/or photoelectrochemical device of the invention comprises a conducting support layer, n-type semiconductor, a light-harvester layer or a sensitizer layer, a hole transporting layer and a counter electrode and/or metal layer. The optoelectronic and/or photoelectrochemical device may comprise an optional surface-increasing scaffold structure. Said metal layer may be doped as well as the n-type semiconductor. A conductive layer comprising a conductive material may be present between the hole transporting layer and the counter electrode and/or metal layer. The hole transporting layer may be provided on the sensitizer layer and is between the sensitizer layer and the conducting current providing layer, if present, or the counter electrode and/or metal layer. Further layer may be present.

According to a further embodiment, the optoelectronic and/or photoelectrochemical device of the invention may comprise a combination of two or more compounds of the invention as hole transporting material. The hole transporting layer may comprise the combination of two or more compounds of the invention.

The optoelectronic and/or photoelectrochemical device of the invention may comprise a hole collector layer, a conductive layer, an electron blocking layer, a sensitizer layer and a current collector layer, wherein the hole collector layer is coated by the conductive layer; wherein the electron blocking layer is between the conductive layer and the sensitizer layer, which is in contact with the current collector layer being a metal or a conductor. The hole collector layer comprises a hole transporting material comprising at least one compound of the invention according to any one of formulae (I), (Ia), (Ib), (Ic), (Id), (Ie) and (If).

The conductive material is selected from one or more conductive polymers or one or more hole transporting materials, which may be selected from poly(3,4-ethylenedioxythiophene):poly(styrenesulfonate) (PEDOT:PSS), poly (3,4-ethylenedioxythiophene):poly(styrenesulfonate): grapheme nanocomposite (PEDOT:PSS:graphene), poly(N-vinylcarbazole) (PVK) and sulfonated poly(diphenylamine) (SPDPA), preferably from PEDOT:PSS, PEDOT:PSS:graphene and PVK, more preferably from PEDOT:PSS. Conductive polymers may also be selected from polymers comprising polyaniline, polypyrrole, polythiophene, polybenzene, polyethylenedioxythiophene, polypropylenedioxythiophene, polyacetylene, and combinations of two or more of the aforementioned, for example.

The conducting support layer is preferably substantially transparent. "Transparent" means transparent to at least a part, preferably a major part of the visible light. Preferably, the conducting support layer is substantially transparent to all wavelengths or types of visible light. Furthermore, the conducting support layer may be transparent to non-visible light, such as UV and IR radiation, for example.

According to an embodiment, the conducting support layer provides the support layer of photovoltaic solid state device. Preferably, the optoelectronic and/or electrochemical device is built on said support layer. The support of the device may be also provided on the side of the counter electrode. In this case, the conductive support layer does not necessarily provide the support of the device, but may simply be or comprise a current collector, for example a metal foil.

The conducting support layer preferably functions and/or comprises a current collector, collecting the current obtained from the device. The conducting support layer may comprise a material selected from indium doped tin oxide (ITO), fluorine doped tinoxide (FTO), $ZnO-Ga_2O_3$, $ZnO-Al_2O_3$, tin-oxide, antimony doped tin oxide (ATO), $SrGeO_3$ and zinc oxide, preferably coated on a transparent substrate, such as plastic or glass. In this case, the plastic or glass provides the support structure of the layer and the cited conducting material provides the conductivity. Such support layers are generally known as conductive glass and conductive plastic, respectively, which are thus preferred conducting support layers in accordance with the invention. The conducting support layer comprises a conducting transparent layer, which may be selected from conducting glass and from conducting plastic.

The surface-increasing scaffold structure is provided on said conducting support structure or on a protective layer that may be provided on said scaffold structure. The surface-increasing scaffold structure is nanostructured and/or mesoporous.

The scaffold structure is made from and/or comprises a metal oxide. For example, the material of the scaffold structure is selected from semiconducting materials, such as Si, $TiO_2$, $SnO_2$, $ZrO_2$, $Al_2O_3$, $Fe_2O_3$, ZnO, $WO_3$, $Nb_2O_5$, CdS, ZnS, PbS, $Bi_2S_3$, CdSe, CdTe, $SrTiO_3$, GaP, InP, GaAs, $CuInS_2$, $CuInSe_2$, and combinations thereof, for example. Preferred semiconductor materials are Si, $TiO_2$, $SnO_2$, ZnO, $WO_3$, $Nb_2O_5$ and $SrTiO_3$, for example. According to an embodiment, the surface-increasing scaffold structure is nanostructured and/or nanoporous.

The invention does not intend to exclude the possibility that there are one or more intermediate layers between the scaffold structure and the conductive support. Such intermediate layers, if present, would preferably be conducting and/or semiconducting.

According to an embodiment, the sensitizer layer of the optoelectronic and/or photoelectrochemical device comprising at least one pigment being selecting from organic, inorganic, organometallic and organic-inorganic pigments or a combination thereof. The sensitizer is preferably a light absorbing compound or material. Preferably, the sensitizer is a pigment, and most preferably the sensitizer is an organic-inorganic pigment.

The sensitizer layer or light-harvester layer may comprise one or more pigments of the group consisting of organometallic sensitizing compounds (phthalocyanine derived compounds, porphyrine derived compounds), metal free organic sensitizing compounds (diketopyrrolopyrrole (DPP) based sensitizer), inorganic sensitizing compounds such as quantum dots, $Sb_2S_3$(Antimonysulfide, for example in the form of thin films), aggregates of organic pigments, nanocomposites, in particular organic-inorganic perovskites, and combinations of the aforementioned.

In an embodiment, the optoelectronic and/or photoelectrochemical device is selected from a photovoltaic solid state device or a solar cell comprising an inorganic perovskite or an organic-inorganic perovskite as sensitizer. In a preferred embodiment, the sensitizer is an organic-inorganic perovskite.

Further the optoelectronic and/or photoelectrochemical device is selected from a photovoltaic solid state device or a solar cell comprising an organic-inorganic perovskite as sensitizer under the form of a layer.

The light-harvester layer or the sensitizer layer comprises, consists of or is made of an organic-inorganic perovskite. Said organic-inorganic perovskite is provided under a film of one perovskite pigment or mixed perovskite pigments or perovskite pigments mixed with further dyes or sensitizers.

The sensitizer layer may comprise a further pigment in addition to the organic-inorganic perovskite pigment, said further pigment selected from organic pigment, organometallic pigment or inorganic pigment.

The term "perovskite", for the purpose of this specification, refers to the "perovskite structure" and not specifically to the perovskite material, $CaTiO_3$. For the purpose of this specification, "perovskite" encompasses and preferably relates to any material that has the same type of crystal structure as calcium titanium oxide and of materials in which the bivalent cation is replaced by two separate monovalent cations. The perovskite structure has the general stoichiometry $WMX_3$, where "W" and "M" are cations and "X" is an anion. The "W" and "M" cations can have a variety of charges and in the original Perovskite mineral ($CaTiO_3$), the W cation is divalent and the M cation is tetravalent. For the purpose of this invention, the perovskite formulae includes structures having three (3) or four (4) anions, which may be the same or different, and/or one or two (2) organic cations, and/or metal atoms carrying two or three positive charges, in accordance with the formulae presented elsewhere in this specification.

The optoelectronic and/or photoelectrochemical device of the invention may comprise one or more layers of an organic-inorganic perovskite. In said device, the last upper layer of organic-inorganic perovskite is coated by the hole transporting layer comprising a hole transporting material as defined above, preferably comprising at least one compound according to any one of formulae (I), (Ia), (Ib), (Ic), (Id), (Ie) and (If).

In an embodiment, the optoelectronic and/or photoelectrochemical device of the invention, wherein the organic-inorganic perovskite layer material comprises a perovskite-structure according any one of formulae (II), (IIa), (IIb), (IIc), (IId) and (IIe) below:

$$WW'MX_4 \quad (II)$$

$$WMX_3 \quad (IIa)$$

$$WW'N_{2/3}X_4 \quad (IIb)$$

$$WN_{2/3}X_3 \quad (IIc)$$

$$BN_{2/3}X_4 \quad (IId)$$

$$BMX_4 \quad (IIe),$$

wherein
W and W' are organic, monovalent cations that are independently selected from primary, secondary, tertiary or quaternary organic ammonium compounds, including N-containing heterorings and ring systems, W and W' having independently from 1 to 60 carbons and 1 to 20 heteroatoms;
B is an organic, bivalent cation selected from primary, secondary, tertiary or quaternary organic ammonium compounds having from 1 to 60 carbons and 2-20 heteroatoms and having two positively charged nitrogen atoms; M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$;
N is selected from the group of $Bi^{3+}$ and $Sb^{3+}$; and,
X is independently selected from $Cl^-$, $Br^-$, $I^-$, $NCS^-$, $CN^-$, $BF_4^-$, $PF_6^-$, $CNO^-$, $SeCN^-$, and $NCO^-$.

In particular, the three or four X may be identical or different. For example, in $WMX_3$ (formula IIa) may be expressed as formula (IIa') below:

$$WMX_iX_{ii}X_{iii} \quad (IIa')$$

wherein Xi, Xii, Xiii are independently selected from $Cl^-$, $Br^-$, $I^-$, $NCS^-$, $CN^-$, $^-$, $BF_4^-$, $PF_6^-$, $CNO^-$, $SeCN^-$, and $NCO^-$, preferably from halides ($Cl^-$, $Br^-$, $I^-$), and W and M are as defined elsewhere in this specification. Xi, Xii, Xiii may thus be the same or different in this case.

Preferably, if Xi, Xii, Xiii in formulae (IIa) and (IIc) or Xi, Xii, Xiii, Xiv in formulae (II), (IIb), (IId) or (IIe) comprise different anions X, there are not more than two different anions. For example, Xi and Xii being the same with Xiii being an anion that is different from Xi and Xii.

According to a preferred embodiment, said organic-inorganic perovskite layer comprises a perovskite-structure according to any one of the formulae (IIf) to (III):

$$WPbX_3 \quad (IIf)$$

$$WSnX_3 \quad (IIg)$$

$$WBiX_4 \quad (IIh)$$

$$WW'PbX_4 \quad (IIi)$$

$$WW'SnX_4 \quad (IIj)$$

$$BPbX_4 \quad (IIk)$$

$$BSnX_4 \quad (III)$$

wherein W, W', B and X are as defined above in this specification. Preferably, X is preferably selected from $Cl^-$, $Br^-$ and $I^-$, most preferably X is $I^-$ or a mixture of $Br^-$ and $I^-$.

According to a preferred embodiment, said organic-inorganic perovskite layer comprises a perovskite-structure of the formulae (IIf) to (III), more preferably (IIf) and/or (IIg) above.

According to an embodiment, W and W' are monovalent cations selected independently from any one of the compounds of formulae (20) to (28) below:

(20)

(21)

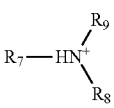
(22)

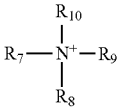
(23)

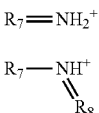
(24)

(25)

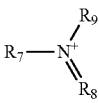
(26)

(27)
$$R_7=N^+=R_8$$

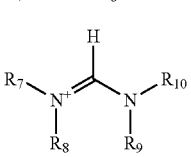
(28)

wherein,
$R_7$, $R_8$, $R_9$ and $R_{10}$ is independently selected from C1-C15 organic substituents comprising from 0 to 15 heteroatoms.

According to an embodiment of said C1-C15 organic substituent any one, several or all hydrogens in said substituent may be replaced by halogen and said organic substituent may comprise up to fifteen (15) N, S or O heteroatoms, and wherein, in any one of the compounds (20) to (28), the two or more of substituents present ($R_7$, $R_8$, $R_9$ and $R_{10}$, as applicable) may be covalently connected to each other to form a substituted or unsubstituted ring or ring system. Preferably, in a chain of atoms of said C1-C15 organic substituent, any heteroatom is connected to at least one carbon atom. Preferably, neighboring heteroatoms are absent and/or heteroatom-heteroatom bonds are absent in said C1-C15 organic substituent comprising from 0 to 15 heteroatoms. The heteroatoms may be selected from N, S, and/or O.

According to an embodiment, $R_7$, $R_8$, $R_9$ and $R_{10}$ are independently selected from C1 to C15 aliphatic and C4 to C15 aromatic or heteroaromatic substituents, wherein any one, several or all hydrogens in said substituent may be replaced by halogen and wherein, in any one of the compounds (20) to (28), the two or more of the substituents present may be covalently connected to each other to form a substituted or unsubstituted ring or ring system.

According to a preferred embodiment, the organic-inorganic perovskite in the device of the invention is selected from a compound of formula (II) or (IIa).

According to an embodiment, B is a bivalent cation selected from any one of the compounds of formulae (49) and (50) below:

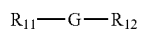

(29)

(30)

wherein, in the compound of formula (29), G is an organic linker structure having 1 to 10 carbons and 0 to 5 heteroatoms selected from N, S, and/or O, wherein one or more hydrogen atoms in said G may be replaced by halogen;

wherein $R_{11}$ and $R_{12}$ are independently selected from a compounds of any one of formulae (20) to (28); and wherein, in the compound of formula (30), the circle containing said two positively charged nitrogen atoms represents a substituted or unsubstituted aromatic ring or ring system comprising 4 to 15 carbon atoms and 2 to 7 heteroatoms or 4 to 10 carbon atoms and 2 to 5 heteroatoms, wherein said nitrogen atoms are ring heteroatoms of said ring or ring system, and wherein the remaining of said heteroatoms may be selected independently from N, O and S and wherein $R_{13}$ and $R_{14}$ are independently selected from H and from a compounds of any one of formulae (20) to (28). Halogen atom substituting hydrogen atom totally or partially may also be present in addition to and/or independently of said 2 to 7 heteroatoms.

Preferably, if the number of carbons is in G is impair, the number of heteroatoms is smaller than the number of carbons. Preferably, in the ring structure of formula (30), the number of ring heteroatoms is smaller than the number of carbon atoms. According to an embodiment, G is an aliphatic, aromatic or heteroaromatic linker structure having from 1 to 10 carbons.

According to an embodiment, $R_7$, $R_8$, $R_9$ and $R_{10}$ are independently selected from C1 to C10 alkyl, C2 to C10 alkenyl, C2 to C10 alkynyl, C4 to C10 heteroaryl and C6 to C10 aryl, wherein said alkyl, alkenyl, and alkynyl, if they comprise 3 or more carbons, may be linear, branched or cyclic, wherein said heteroaryl and aryl may be substituted or unsubstituted, and wherein several or all hydrogens in $R_7$, $R_8$, $R_9$ and $R_{10}$ may be replaced by halogen.

According to an embodiment, $R_7$, $R_8$, $R_9$ and $R_{10}$ are independently selected from C1 to C8 alkyl, C2 to C8 alkenyl, C2 to C8 alkynyl, C4 to C8 heteroaryl and C6 to C8 aryl, wherein said alkyl, alkenyl, and alkynyl, if they comprise 3 or more carbons, may be linear, branched or cyclic, wherein said heteroaryl and aryl may be substituted or unsubstituted, and wherein several or all hydrogens in $R_7$, $R_8$, $R_9$ and $R_{10}$ may be replaced by halogen.

According to an embodiment, $R_7$, $R_8$, $R_9$ and $R_{10}$ are independently selected from C1 to C6 alkyl, C2 to C6 alkenyl, C2 to C6 alkynyl, C4 to C6 heteroaryl and C6 aryl, wherein said alkyl, alkenyl, and alkynyl, if they comprise 3 or more carbons, may be linear, branched or cyclic, wherein said heteroaryl and aryl may be substituted or unsubstituted, and wherein several or all hydrogens in $R_7$, $R_8$, $R_9$ and $R_{10}$ may be replaced by halogen.

According to an embodiment, $R_7$, $R_8$, $R_9$ and $R_{10}$ are independently selected from C1 to C4 alkyl, C2 to C4 alkenyl and C2 to C4 alkynyl, wherein said alkyl, alkenyl and alkynyl, if they comprise 3 or more carbons, may be linear, branched or cyclic, and wherein several or all hydrogens in $R_7$, $R_8$, $R_9$ and $R_{10}$ may be replaced by halogen.

According to an embodiment, $R_7$, $R_8$, $R_9$ and $R_{10}$ are independently selected from C1 to C3, preferably C1 to C2 alkyl, C2 to C3, preferably C2 alkenyl and C2 to C3, preferably C2 alkynyl, wherein said alkyl, alkenyl and alkynyl, if they comprise 3 or more carbons, may be linear, branched or cyclic, and wherein several or all hydrogens in $R_7$, $R_8$, $R_9$ and $R_{10}$ may be replaced by halogen.

According to an embodiment, $R_7$, $R_8$, $R_9$ and $R_{10}$ is independently selected from C1 to C4, more preferably C1 to C3 and even more preferably C1 to C2 alkyl. Most preferably $R_7$, $R_8$, $R_9$ and $R_{10}$ are methyl. Again, said alkyl may be completely or partially halogenated.

According to an embodiment, W, W' and B are monovalent (W, W') and bivalent (B) cations, respectively, selected from substituted and unsubstituted C5 to C6 rings comprising one, two or more nitrogen heteroatoms, wherein one (for W and W') or two (for B) of said nitrogen atoms is/are positively charged. Substituents of such rings may be selected from halogen and from C1 to C4 alkyls, C2 to C4 alkenyls and C2 to C4 alkynyls as defined above, preferably from C1 to C3 alkyls, C3 alkenyls and C3 alkynyls as defined above. Said ring may comprise further heteroatoms, which may be selected from O, N and S. Bivalent organic cations B comprising two positively charged ring N-atoms are exemplified, for example, by the compound of formula (30) above. Such rings may be aromatic or aliphatic.

W, W' and B may also comprise a ring system comprising two or more rings, at least one of which being from substituted and unsubstituted C5 to C6 ring as defined as above. The elliptically drawn circle in the compound of formulae (30) may also represent a ring system comprising, for example, two or more rings, but preferably two rings. Also if W and/or W' comprises two rings, further ring heteroatoms may be present, which are preferably not charged, for example.

According to an embodiment, however, the organic cations W, W' and B comprise one (for W, W'), two (for B) or more nitrogen atom(s) but are free of any O or S or any other heteroatom, with the exception of halogens, which may substitute one or more hydrogen atoms in cation W and/or B.

W and W' preferably comprise one positively charged nitrogen atom. B preferably comprises two positively charged nitrogen atoms.

W, W' and B may be selected from the exemplary rings or ring systems of formulae (31) and (32) (for W, W') and from (33) to (35) (for B) below:

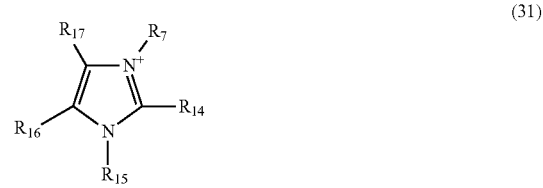

(31)

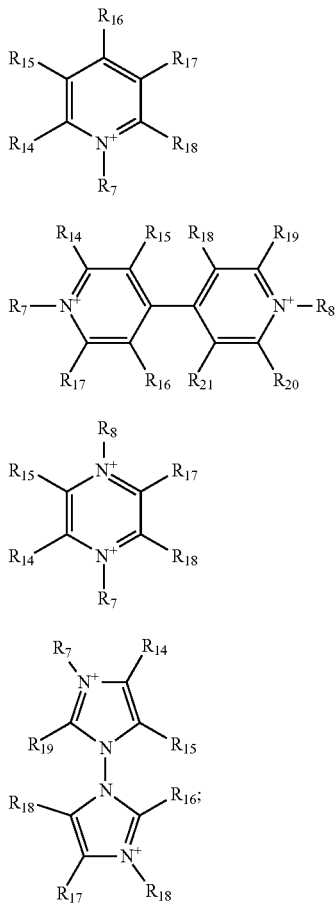

wherein

R₇ and R₈ are selected from substituents as defined above, and R₁₄, R₁₅, R₁₆, R₁₇, R₁₈, R₁₉, R₂₀ and R₂₁ are independently selected from H, halogen and substituents as defined above for R₇, R₈, R₉ and R₁₀. Preferably, R₁₄, R₁₅, R₁₆, R₁₇, R₁₈, R₁₉, R₂₀ and R₂₁ are selected from H and halogen, most preferably H.

In the organic cations W, W' and B, hydrogen atoms may be substituted by halogens, such as F, Cl, I, and Br, preferably F or Cl. Such a substitution is expected to reduce the hygroscopic properties of the perovskite layer or layers and may thus provide a useful option for the purpose of the present specification.

According to a preferred embodiment, W and W' are independently selected from organic cations of formula (20) and/or formula (28).

According to a preferred embodiment, the metal M is selected from $Sn^{2+}$ and $Pb^{2+}$, preferably $Pb^{2+}$. According to a preferred embodiment, N is $Sb^{3+}$.

According to a preferred embodiment, the three or four X are independently selected from Cl⁻, Br⁻, and I⁻.

In a further aspect, the invention provides use of the compound of the invention as a tuner of HOMO level.

The present invention will now be illustrated by way of examples. These examples do not limit the scope of this invention, which is defined by the appended claims.

EXAMPLES

Example 1: Synthesis of Functionalized Spirofluorene Derivatives According to the Invention Spiro compounds HT-SO2, HT-SO07, HT-SO8, HT-SO09, HT-SO10 (FIG. 1E) comprise a diarylamino functionalized fluorene moiety and a cyclopenta[2,1-b:3,4-b']dithiophene unit sharing a common sp³-hybridized carbon atom.

Only a few examples of related mixed spiro compounds, devoid of electron-donating diarylamino substituents on the fluorene portion of the molecule, have been disclosed so far and their synthesis proved to be cumbersome. Indeed, considerable amounts of by-products are formed when the intramolecular ring closure leading to the formation of the spiro linkage is carried out on 2,2'-bithiophene derivatives under standard acidic conditions. Low yields after extensive purification of complex reaction mixtures have been thus reported. It has been recently shown that the introduction of protecting groups on the electron-rich α-positions of the thiophene units, in combination with the use of suitable Lewis acids, markedly increases the efficiency of the intramolecular cyclization process. Based on these considerations, we have developed two viable synthetic routes towards diarylamino functionalized fluorene-bithiophene spiro compounds, which differ in the stage of introduction of the diarylamino groups and are outlined in FIG. 1A.

Both strategies were explored in the case of HT-SO2 and the synthetic details are here summarized. Following strategy A (FIG. 1A and FIG. 1B), palladium catalysed coupling reaction between 2,7-dibromofluoren-9-one 1 and bis(4-methoxyphenyl)amine 2 allowed to introduce two diarylamino substituents onto the fluorene moiety at the first stage (Scheme 2). 2,7-Bis(bis(4-methoxyphenyl)amino)fluoren-9-one 3 was thus isolated in excellent yield. Subsequent reaction of 3 with the carbanion generated by treatment of 3-bromo-5,5'-bis(trimethylsilyl)-2,2'-bithiofene 4 with BuLi at low temperature afforded the tertiary alcohol 5 in 75% yield.

Intramolecular Friedel-Craft cyclization of 5 was performed in refluxing chloroform in the presence of FeCl₃ as Lewis acid according to a procedure previously devised for the synthesis of 4,4'-spirobi(cyclopenta(2,1-b:3,4-b')dithiophene) derivatives [2]. Complete removal of the TMS protecting groups was ensured by post-reaction treatment of the chloroform solution with trifluoroacetic acid and the desired product HT-SO2 could be readily isolated by column chromatography on silica in 66% yield (overall yield from 1=46.5%).

Following strategy B (FIG. 1A and FIG. 1C), bithiophene derivative 4 was treated with BuLi at low temperature and then reacted with 2,7-dibromofluoren-9-one 1 to give carbinol 6 in 80% yield (Scheme 3). Intramolecular cyclization mediated by FeCl₃ was effective also for this derivative, affording the key intermediate 7 in 80% yield. Finally, the targeted compound HT-SO02 was obtained by palladium catalysed reaction of 7 with bis(4-methoxyphenyl)amine 2 in 81% yield (overall yield from 1=51%).

Strategies A and B here described are both suitable for the preparation of the targeted compounds. The second one seems to be preferable because the presence of two bromine atoms on the preformed spiro compound 7 opens the way to a variety of promising structural modifications through well-established synthetic procedures. To explore this option, 7 was used as the common intermediate in the preparation of mixed fluorene/bithiophene spiro derivatives by palladium catalysed amination reaction with different diarylamines (FIG. 1D). Compounds HT-SO7, HT-SO8, HT-SO9 and HT-SO10 (FIG. 1E) were thus obtained in good to excellent yields, ranging from 64 to 90%.

All available chemicals were purchased from commercial sources and were used without any further purification. Solvents were purified by standard methods and dried if necessary. 3-Bromo-5,5'-bis(trimethylsilyl)-2,2'-bithiofene 4 were prepared as previously described. 2,7-Bis(bis(4-methoxyphenyl)amino)-fluoren-9-one 3 was prepared according to a modification of the original literature procedure [4]. Para-substituted diarylamines were synthesized according to a two-step procedure [5] involving the Ulmann-like coupling of two equivalents of para-substituted aryliodide with BocNH$_2$, followed by deprotection of the Ar$_2$N-Boc intermediate under acidic conditions. Reactions were monitored by thin layer chromatography (TLC) that was conducted on plates precoated with silica gel Si 60-F254 (Merck, Germany). Column chromatography was conducted using silica gel Si 60, 0.063-0.200 mm (normal) or 0.040-0.063 mm (flash) (Merck, Darmstadt, Germany). $^1$H and $^{13}$C NMR spectra were recorded on a Bruker Avance 400 (400 and 100.6 MHz, respectively); chemical shifts are indicated in parts per million downfield from SiMe$_4$, using the residual proton (CHCl$_3$=7.26 ppm) and carbon (CDCl$_3$=77.0 ppm) solvent resonances as the internal reference. Protons and carbon assignments were achieved by $^{13}$C-APT, $^1$H-$^1$H COSY, and $^1$H-$^{13}$C heteronuclear correlation experiments. Coupling constant values J are given in Hz.

Figure 1B:
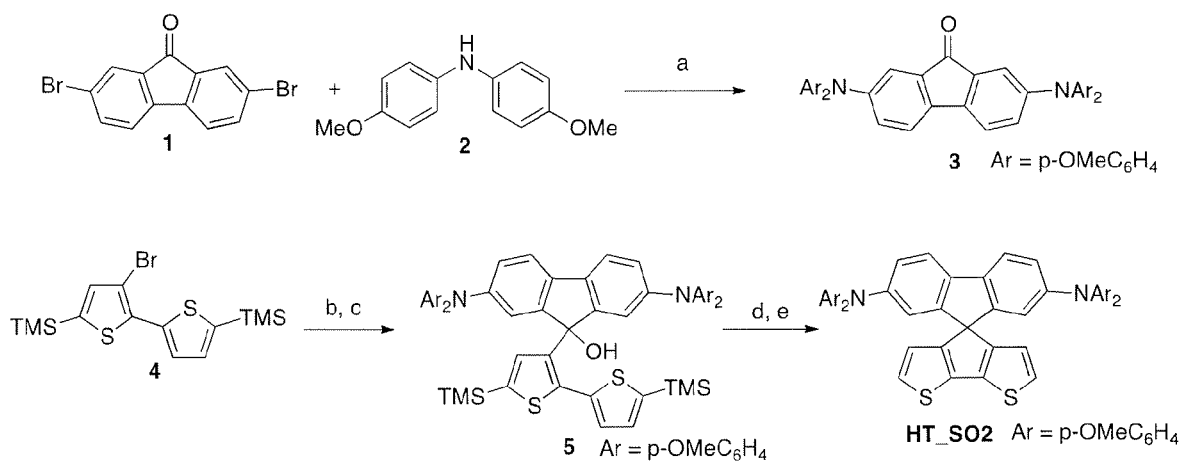
FIG. 1B shows scheme of strategy A: a: $Pd_2(dba)_3$, $tBu_3P$, $NaO^tBu$, toluene, 110° C., 94%; b: BuLi, $Et_2O$, −78° C.; c: 3, THF, −78° C.→rt, 75%; d: $FeCl_3$, $CHCl_3$, reflux; e: TFA, $CHCl_3$, rt, 66%.

Synthesis of HT-SO2 (FIG. 1A)

2,7-Bis(bis(4-methoxyphenyl)amino)fluoren-9-one 3

In a flame dried Schlenk tube 2,7-dibromofluoren-9-one 1 (1 g, 2.96 mmol), bis(4-methoxyphenyl)amine 2 (1.47 g, 6.41 mmol) and Pd$_2$(dba)$_3$ (100 mg, 0.11 mmol) were introduced under inert atmosphere. The Schlenk tube was evacuated and backfilled with nitrogen three times. After the addition of toluene (16 mL) and tBu$_3$P (1M toluene solution, 110 μL, 0.11 mmol), NaO$^t$Bu (600 mg, 6.24 mmol) was added and the reactor was brought into an oil bath pre-heated at 110° C. The reaction mixture was stirred at this temperature overnight. After cooling to rt, the solvent was removed at reduced pressure, the residue was taken up in CH$_2$Cl$_2$ and washed with water and brine. The organic phase was dried over MgSO$_4$, filtered and the solvent removed at reduced pressure. The crude material was suspended in MeOH and refluxed for 1 h. After cooling, the mixture was filtered on Buchner funnel. The solid was washed with methanol and dried under reduced pressure to give the title compound (1.76 g, 94% yield) as a blue solid whose spectral data are in agreement with those reported in the literature.

$^1$H NMR (400 MHz, DMSO-d$_6$): δ 7.32 (d, J=8.0 Hz, 2H, Fluor-H), 7.04 (d, J=8.8 Hz, 8H, Ar—H), 6.92 (d, J=8.8 Hz, 8H, Ar—H), 6.81 (dd, J=8.0 Hz, J=2.4 Hz, 2H, Fluor-H), 6.76 (d, J=2.4 Hz, 2H, Fluor-H), 3.73 (OCH$_3$); $^{13}$C NMR (100.6 MHz, DMSO-d$_6$): δ 193.7 (CO), 156.6, 149.1, 139.9, 136.0, 135.0, 127.6 (Ar—C), 124.5 (Fluor-C), 121.4 (Fluor-C), 115.6 (Ar—C), 114.3 (Fluor-C), 55.7 (OCH$_3$).

2,7-Bis(bis(4-methoxyphenyl)amino)-9-(5,5'-bis(trimethylsilyl)-2,2'-bithiophen-3-yl)fluoren-9-ol 5

To a solution of 3-bromo-5,5'-bis(trimethylsilyl)-2,2'-bithiofene 4 (419.7 mg, 1.08 mmol) in dry Et$_2$O (16 mL) cooled to −78° C., BuLi (1.6 M in hexane, 670 μL, 1.07 mmol) was added dropwise under stirring. After 1 h a solution of ketone 3 (555.8 mg, 0.87 mmol) in dry THF (10 mL) was added dropwise. At the end of the addition, the cooling bath was removed and mixture was allowed to return to rt and left under stirring overnight. After the addition of a solution of saturated NH$_4$Cl and phase separation, the organic layer was washed with water, brine and dried over MgSO$_4$. After filtration, the solvent was removed at reduced pressure and the crude material was purified by column chromatography (silica gel, petroleum ether:Et$_2$O 6:4) affording the title compound (620 mg, 75% yield) as brown foam.

$^1$H NMR (400 MHz, CDCl$_3$+1% v/v NH$_2$NH$_2$.H$_2$O): δ 7.47 (br s, 1H, Thioph-H), 7.09 (d, J=8.0 Hz, 2H, Fluor-H), 6.96 (d, J=8.4 Hz, 8H, Ar—H), 6.90 (d, J=2.0 Hz, 2H, Fluor-H), 6.80-6.75 (m, 11H, Ar—H, Fluor-H, Thioph-H), 6.29 (d, J=2.8 Hz, 2H, Thioph-H), 0.27 (s, 9H, SiCH$_3$), 0.26 (s, 9H, SiCH$_3$); $^{13}$C NMR (100.6 MHz, CDCl$_3$+1% v/v NH$_2$NH$_2$—H$_2$O): δ 155.5, 150.4, 148.0, 142.0, 141.6, 141.2, 139.2, 139.1, 135.2, 135.1 (Thioph-C), 133.0 (Thioph-C), 129.5 (Thioph-C), 126.0 (Ar—C), 122.3 (Fluor-C), 119.5 (Fluor-C), 118.0 (Fluor-C), 114.6 (Ar—C), 82.1, 55.5 (OCH$_3$), 0.1 (Si—CH$_3$), 0.0 (Si—CH$_3$).

2',7'-Bis(bis(4-methoxyphenyl)amino)spiro[cyclopenta[2,1-b:3,4-b']dithiophene-4,9'-fluorene] HT-SO2

To boiling CHCl$_3$ (amylene stabilised, 20 mL) containing FeCl$_3$ (2.5 mg, 0.015 mmol), carbinol 5 (54.8 mg, 0.058 mmol) was added and the dark red solution was refluxed under stirring until the disappearance of the starting material was confirmed by TLC analysis (silica gel, Petroleum ether:Et$_2$O 6:4). After cooling, TFA (0.2 mL) was added and the mixture was stirred at rt for 20 min and then concentrated at reduced pressure. The residue was taken up in CH$_2$C$_2$, washed with saturated aqueous NaHCO$_3$ solution, water and brine and dried over MgSO$_4$. After filtration, the solvent was removed at reduced pressure and the crude was purified by column chromatography (silica gel, petroleum ether:Et$_2$O 8:2) affording the title compound (30 mg, 66%) as an off-white solid.

$^1$H NMR (400 MHz, CDCl$_3$+1% v/v NH$_2$NH$_2$.H$_2$O): δ 7.44 (d, J=8.4 Hz, 2H, Fluor-H), 7.05 (d, J=5.2 Hz, 2H, Thioph-H), 6.88 (d, J=9.2 Hz, 8H, Ar—H), 6.82 (dd, J=8.4 Hz, J=2.0 Hz, 2H, Fluor-H), 6.69 (d, J=9.2 Hz, 8H, Ar—H), 6.51 (d, J=5.2 Hz, 2H, Thioph-H), 6.47 (d, J=2.0 Hz, 2H, Fluor-H), 3.74 (s, 12H, OCH$_3$); $^{13}$C NMR (100.6 MHz, CDCl$_3$+1% v/v NH$_2$NH$_2$H$_2$O): δ 155.3, 154.9, 147.3, 146.1, 141.2, 138.2, 135.0, 125.6 (Ar—C), 125.2 (Thioph-C), 121.7 (Fluor-C), 121.3 (Thioph-C), 119.6 (Fluor-C), 116.9 (Fluor-C), 114.4 (Ar—C), 61.7, 55.5 (OCH$_3$).

Figure 1C:
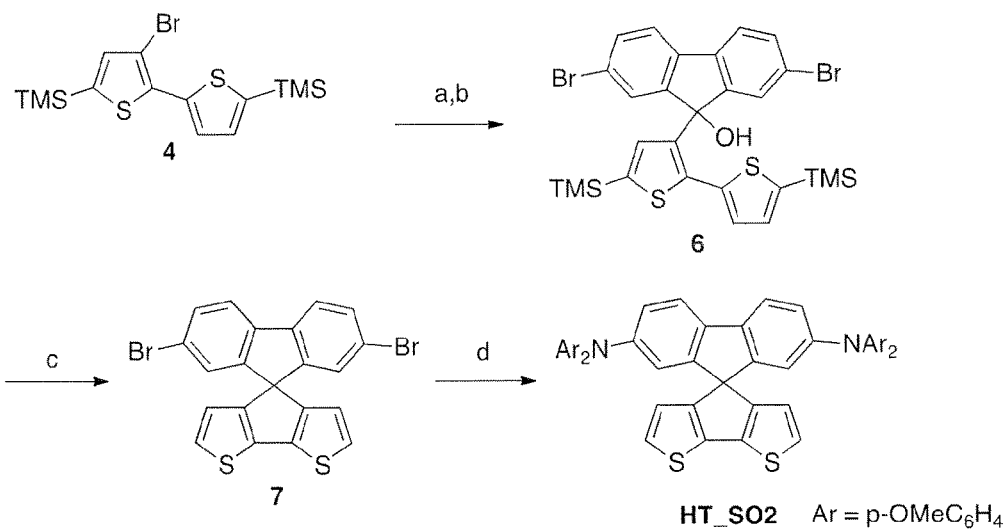
FIG. 1C shows scheme of strategy B: a: BuLi, $Et_2O$, −78° C.; b: 1, THF, −78° C.→rt, 80%; c: $FeCl_3$, $CHCl_3$, reflux, 80% or AcOH, HCl, reflux, 79%; d: $Pd_2(dba)_3$, $^tBu_3P$, $NaO^tBu$, toluene, 110° C., 81%.
Figure 1D:
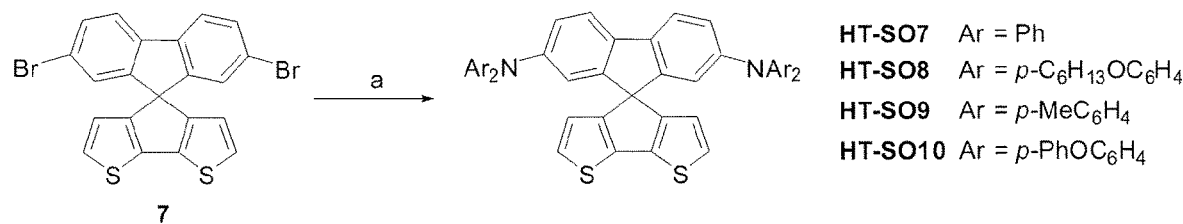
FIG. 1D shows scheme of synthesis of compounds of invention from spiro compound 7 preformed in strategy B: a: $Ar_2NH$, $Pd_2(dba)_3$, $^tBu_3P$, $NaO^tBu$, toluene, 110° C.
Figure 1E:
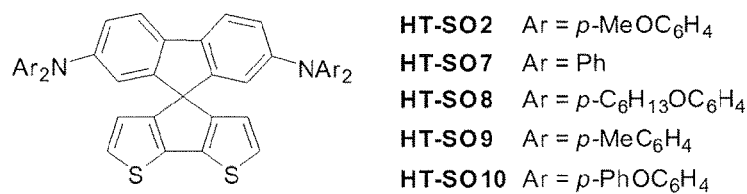
FIG. 1E shows the specific structures of compounds of the invention being HT-SO2, HT-SO7, HT-SO8, HT-SO9, HT-SO10.

Synthesis of HT-SO2 (FIG. 1C)

9-(5,5'-Bis(trimethylsilyl)-2,2'-bithiophen-3-yl)-2,7-dibromo-fluoren-9-ol 6

To a solution of protected dithiophene 4 (1.54 g, 3.95 mmol) in dry Et$_2$O (50 mL) cooled to −78° C., BuLi (1.6 M in hexane, 2.5 mL, 4 mmol) was added dropwise under stirring. After 2 h, a solution of ketone 3 (1.11 g, 3.28 mmol) in dry THF (30 mL) was added dropwise. At the end of the addition, the cooling bath was removed and mixture was allowed to return to rt and left under stirring for 4 h. After the addition of saturated aqueous NH$_4$Cl solution and phase separation, the organic layer was washed with water, brine and dried over MgSO$_4$. After filtration, the solvent was removed at reduced pressure and the crude material was purified by flash column chromatography (silica gel, petroleum ether:CH$_2$Cl$_2$ 7:3) affording the title compound (1.7 g, 80% yield) as an off-white foam.

$^1$H NMR (400 MHz, CDCl$_3$): δ 7.73 (s, 1H, Thioph-H), 7.42 (d, J=1.6 Hz, 2H, Fluor-H), 7.36 (dd, J=8.0 Hz, J=1.6 Hz, 2H, Fluor-H), 7.21 (d, J=8.0 Hz, 2H, Fluor-H), 6.62 (d, J=3.6 Hz, 1H, Thioph-H), 6.03 (d, J=3.6 Hz, 1H, Thioph-H), 0.32 (s, 9H, SiCH$_3$), 0.29 (s, 9H, SiCH$_3$); $^{13}$C NMR (100.6 MHz, CDCl$_3$): δ 151.0, 142.7, 140.7, 140.6, 138.4, 137.8, 136.0, 134.4 (Thioph-C), 133.1 (Thioph-C), 132.3 (Fluor-C), 129.8 (Thioph-C), 128.5 (Fluor-C), 122.3, 121.3 (Fluor-C), 82.0, 0.1 (Si—CH$_3$), 0.0 (Si—CH$_3$);

2',7'-Dibromospiro[cyclopenta[2,1-b:3,4-b']dithiophene-4,9'-fluorene] 7 Lewis Acid Mediated Cyclization to boiling CHCl$_3$ (amylene stabilised, 250 mL) carbinol 6 (560 mg, 0.86 mmol) and FeCl$_3$ (75 mg, 0.46 mmol) was added. The solution became green and after 20 min under stirring the disappearance of starting material was confirmed by TLC analysis (silica gel, Petroleum ether: CH$_2$Cl$_2$ 7:3). The mixture was cooled to rt and the solvent removed at reduced pressure. The crude material was purified by column chromatography (silica gel, petroleum ether:CHCl$_3$ 9:1) to give the title compound (339 mg, 81% yield) as a white solid.

Brønsted Acid Mediated Cyclization:

to boiling AcOH (200 mL) carbinol 6 (500 mg, 0.77 mmol) and concentrated HCl (0.3 mL) were added and the solution was refluxed under stirring for 2 h. After cooling to rt, the solvent was removed at reduced pressure and the residue taken up in AcOEt and washed with aqueous NaOH solution (10%, w/v) and water. The organic phase was dried over MgSO$_4$, filtered and the solvent removed under reduced pressure. The crude material was purified by column chromatography (silica gel, petroleum ether:CHCl$_3$ 9:1) to give the title compound (295 mg, 79% yield) as a white solid.

NMR spectral data for the two samples were identical.

$^1$H NMR (400 MHz, CDCl$_3$): δ 7.63 (d, J=8.4 Hz, 2H, Fluor-H), 7.49 (d, J=8.4 Hz, J=1.6 Hz, 2H, Fluor-H), 7.12 (d, J=5.0 Hz, 2H, Thioph-H), 6.95 (d, J=1.6 Hz, 2H, Fluor-H), 6.41 (d, J=5.0 Hz, 2H, Thioph-H); $^{13}$C NMR (100.6 MHz, CDCl$_3$): δ 152.9, 147.1, 139.5, 138.9, 131.3 (Fluor-C), 126.9 (Thioph-C), 126.1 (Fluor-C), 121.8, 121.5 (Fluor-C), 121.3 (Thioph-C), 61.3.

2',7'-Bis(bis(4-methoxyphenyl)amino)spiro[cyclopenta[2,1-b:3,4-b]dithiophene-4,9'-fluorene] HT-SO2

In a flame dried Schlenk tube the spiro derivative 7 (303.7 mg, 0.62 mmol), bis(4-methoxyphenyl)amine 2 (315.8 mg, 1.38 mmol) and Pd$_2$(dba)$_3$ (22.2 mg, 0.024 mmol) were introduced under inert atmosphere. The Schlenk tube was evacuated and backfilled with nitrogen three times. After the addition of toluene (5 mL) and tBu$_3$P (1 M toluene solution, 25 μL, 0.025 mmol), NaO$^t$Bu (149 mg, 1.55 mmol) was added and the reactor was brought into an oil bath pre-heated at 110° C. The reaction mixture was stirred at this temperature overnight. After cooling to rt, the mixture was diluted with Et$_2$O and washed with water and brine. The organic phase was dried over MgSO$_4$, filtered and the solvent removed at reduced pressure. The crude material was purified by flash column chromatography (silica gel, hexane:AcOEt 8:2) to give the title compound (400 mg, 82% yield) as an off-white solid.

General Procedure for the Amination of 7.

A flame dried Schlenk tube was charged with 7 (1 mmol), diarylamine (2.2 mmol) and Pd$_2$(dba)$_3$ (4 mol %). The Schlenk tube was evacuated and backfilled with nitrogen three times. After the addition of toluene (6 mL) and tBu$_3$P (1M toluene solution, 4 mol %), NaO$^t$Bu (2.5 mmol) was added and the reactor was brought into an oil bath pre-heated at 110° C. The reaction mixture was stirred at this temperature overnight. After cooling to rt, the mixture was diluted with CH$_2$Cl$_2$ and washed with water and brine. The organic phase was dried over MgSO$_4$, filtered and the solvent removed at reduced pressure. The crude material was purified by column chromatography on silica gel.

2',7'-Bis(diphenylamino)spiro[cyclopenta[2,1-:3,4-b']dithiophene-4,9'-fluorene] HT-SO7

This product was obtained according to the general amination procedure starting from 7 (405 mg, 0.83 mmol) and diphenylamine (306 mg, 1.8 mmol). Flash column chromatography (silica gel, hexane:toluene from 9:1 to 8:2) gave the title compound as an off-white solid (500 mg, 91% yield).

$^1$H NMR (400 MHz, CDCl$_3$+1% v/v NH$_2$NH$_2$.H$_2$O): δ 7.56 (d, J=8.4 Hz, 2H, Fluor-H), 7.17-7.13 (m, 8H, Ar—H), 7.06 (d, J=5.2 Hz, 2H, Thioph-H), 6.99-6.91 (m, 14H, Ar—H, Fluor-H), 6.61 (d, J=2.0 Hz, 2H, Fluor-H), 6.53 (d, J=5.2 Hz, 2H, Thioph-H); $^{13}$C NMR (100.6 MHz, CDCl$_3$+1% v/v NH$_2$NH$_2$.H$_2$O): δ 154.5, 147.6, 146.7, 146.5, 138.4, 136.4, 129.1 (Ar—C), 125.5 (Thioph-C), 124.3 (Ar—C), 123.7 (Ar—C), 122.5 (Fluor-C), 121.2 (Thioph-C), 120.1 (Fluor-C), 119.5 (Fluor-C), 61.6.

2',7'-Bis(bis(4-hexylphenyl)amino)spiro[cyclopenta[2,1-b:3,4-b']dithiophene-4,9'-fluorene] HT-SO8

This product was obtained according to the general amination procedure starting from 7 (239.4 mg, 0.49 mmol) and bis(4-hexylphenyl)amine (345.4, 1.02 mmol). Flash column chromatography (silica gel, petroleum ether:CH$_2$Cl$_2$ 100:1) gave the title compound as a pale yellow sticky solid (315 mg, 64% yield).

$^1$H NMR (400 MHz, CDCl$_3$+1% v/v NH$_2$NH$_2$—H$_2$O): δ 7.50 (d, J=8.4 Hz, 2H, Fluor-H), 7.05 (d, J=4.8 Hz, 2H, Thioph-H), 6.95-6.91 (m, 10H, Ar—H, Fluor-H), 6.86 (d, J=8.4 Hz, 8H, Ar—H), 6.57 (d, J=2.0 Hz, 2H, Fluor-H), 6.52 (d, J=4.8 Hz, 2H, Thioph-H), 2.50 (m, 8H, Alk-H), 1.55 (m, 8H, Alk-H), 1.33-1.29 (m, 24H, Alk-H), 0.89 (m, 12H, Alk-H); $^{13}$C NMR (100.6 MHz, CDCl$_3$+1% v/v NH$_2$NH$_2$—H$_2$O): δ 154.7, 147.0, 146.2, 145.3, 138.3, 137.1, 135.8, 128.9 (Ar—C), 125.2 (Thioph-C), 123.6 (Ar—C), 123.5 (Fluor-C), 121.3 (Thioph-C), 119.8 (Fluor-C), 118.8 (Fluor-C), 61.7, 35.3 (Alk-C), 31.8 (Alk-C), 31.5 (Alk-C), 29.0 (Alk-C), 22.7 (Alk-C), 14.2 (Alk-C).

2',7'-Bis(bis(4-methylphenyl)amino)spiro[cyclopenta[2,1-b:3,4-b']dithiophene-4,9'-fluorene] HT-SO9

This product was obtained using the standard amination procedure starting from 7 (300.9 mg, 0.62 mmol) and bis(4-methylphenyl)amine (268.3 mg, 1.36 mmol). Flash column chromatography (silica gel, petroleum ether:CH$_2$Cl$_2$ 9:1) gave the title compound as a pale yellow solid (300 mg, 67% yield).

¹H NMR (400 MHz, CDCl₃+1% v/v NH₂NH₂.H₂O): δ 7.48 (d, J=8.4 Hz, 2H, Fluor-H), 7.05 (d, J=4.8 Hz, 2H, Thioph-H), 6.94 (br d, J=8.4 Hz, 8H, Ar—H), 6.89 (dd, J=8.4 Hz, J=2.4 Hz, 2H, Fluor-H), 6.84 (br d, J=8.4 Hz, 8H, Ar—H), 6.57 (d, J=2.4 Hz, 2H, Fluor-H), 6.52 (d, J=4.8 Hz, 2H, Thioph-H), 2.25 (s, 12H, CH₃); ¹³C NMR (100.6 MHz, CDCl₃+1% v/v NH₂NH₂.H₂O): δ 154.7, 146.9, 146.2, 145.3, 138.3, 135.8, 132.0, 129.7 (Ar—C), 125.3 (Thioph-C), 123.8 (Ar—C), 123.4 (Fluor-C), 121.3 (Thioph-C), 119.8 (Fluor-C), 118.5 (Fluor-C), 61.7, 29.7, 20.8 (CH₃).

2',7'-Bis(bis(4-phenoxyphenyl)amino)spiro[cyclopenta[2,1-b:3,4-b']dithiophene-4,9'-fluorene] HT-SO10

This product was obtained using the standard amination procedure starting from 7 (208 mg, 0.43 mmol) and bis(4-phenoxyphenyl)amine (333.8 mg, 0.94 mmol). Flash column chromatography (silica gel, petroleum ether: AcOEt 95:5) gave the title compound as an off-white solid (330 mg, 75% yield).

¹H NMR (400 MHz, CDCl₃+1% v/v NH₂NH₂.H₂O): δ 7.54 (d, J=8.0 Hz, 2H, Fluor-H), 7.33-7.26 (m, 8H, PhO—H), 7.08-7.02 (m, 6H, PhO—H, Thioph-H), 6.99-6.93 (m, 18H, Fluor-H, PhO—H, Ar—H), 6.81 (d, J=8.8 Hz, 8H, Ar—H), 6.52 (d, J=2.0 Hz, 2H, Fluor-H), 6.49 (d, J=5.2 Hz, 2H, Thioph-H); ¹³C NMR (100.6 MHz, CDCl₃+1% v/v NH₂NH₂.H₂O): δ 157.7, 154.7, 152.1, 147.0, 146.4, 143.3, 138.3, 135.9, 129.7 (PhO—C), 125.5 (Thioph-C), 125.2 (Ar—C), 123.1 (Fluor-C), 122.9 (PhO—C), 121.2 (Thioph-C), 120.0, 119.9 (Ar—C), 118.5 (Fluor-C), 118.3 (Ar—C), 61.6;

Example 2: Synthesis of Solar Cell Having Mixed Fluoren/Bithiopene Spiro Derivatives Substrate Preparation and Li-Doping TiO₂

Nippon Sheet Glass 10 Ω/sq was cleaned by sonication in 2% Hellmanex water solution for 30 minutes. After rinsing with deionised water and ethanol, the substrates were further cleaned with UV ozone treatment for 15 min. Then, 30 nm TiO2 compact layer was deposited on FTO via spray pyrolysis at 450° C. from a precursor solution of titanium diisopropoxide bis(acetylacetonate) in anhydrous ethanol. After the spraying, the substrates were left at 450° C. for 45 min and left to cool down to room temperature. Then, mesoporous TiO₂ layer was deposited by spin coating for 20 s at 4000 rpm with a ramp of 2000 rpm s-1, using 30 nm particle paste (Dyesol 30 NR-D) diluted in ethanol to achieve 150-200 nm thick layer. After the spin coating, the substrates were immediately dried at 100° C. for 10 min and then sintered again at 450° C. for 30 min under dry air flow. Li-doping of mesoporous TiO2 is accomplished by spin coating a 0.1 M solution of Li-TFSI in acetonitrile at 3000 rpm for 30 s followed by another sintering step at 450° C. for 30 minutes. After cooling down to 150° C. the substrates were immediately transferred in a nitrogen atmosphere glove box for depositing the perovskite films.

Perovskite Precursor Solution and Film Preparation

The perovskite films were deposited from a precursor solution containing FAI (1 M) (formamidinium iodide), PbI2 (1.1 M), MABr (0.2 M) (methylammonium iodide) and PbBr2 (0.2 M) in anhydrous DMF:DMSO 4:1 (v:v). The perovskite solution was spin coated in a two steps program at 1000 and 4000 rpm for 10 and 30 s respectively. During the second step, 100 μL of clorobenzene was poured on the spinning substrate 15 s prior the end of the program. This perovskite is referred to as the "mixed perovskite".

Another perovskite type, referred to as "standard perovskite", was prepared by dissolving a stoichiometric amount (1:1 molar ratio) of lead iodide and methyl ammonium iodide in dimethylsulfoxide at a concentration of 1.2 M of each component.

The substrates were then annealed at 100° C. for 1 h in a nitrogen filled glove box.

Hole Transporting Layer and Top Electrode

After the perovskite annealing the substrates were cooled down for few minutes and a spirofluorene linked methoxy triphenylamines (spiro-OMeTAD, Merck) solution (70 mM in chlorobenzene) was spin coated at 4000 rpm for 20 s. The spiro-OMeTAD was doped with bis(trifluoromethylsulfonyl)imide lithium salt (Li-TFSI, Sigma-Aldrich), tris(2-(1H-pyrazol-1-yl)-4-tert-butylpyridine)-cobalt(III) tris(bis(trifluoromethylsulfonyl)imide) (FK209, Dynamo) and 4-tert-Butylpyridine (TBP, Sigma-Aldrich). The molar ratio of additives for spiro-OMeTAD was: 0.5, 0.03 and 3.3 for Li-TFSI, FK209 and TBP respectively.

SO solutions were prepared with molarities ranging from 50-150 mM (in chlorobenzene). The optimised molar ratio of additives for SO2 was: 0.5, 0.03 and 3.3 for Li-TFSI, FK209 and TBP respectively. The SO solution was spin coated at 4000 rpm for 20 s.

Finally 70-80 nm of gold top electrode was thermally evaporated under high vacuum.

Photovoltaic Device Testing

The solar cells were measured using a 450 W xenon light source (Oriel). The spectral mismatch between AM1.5G and the simulated illumination was reduced by the use of a Schott K113 Tempax filter (Priizisions Glas & Optik GmbH). The light intensity was calibrated with a Si photodiode equipped with an IR-cutoff filter (KG3, Schott) and it was recorded during each measurement. Current-voltage characteristics of the cells were obtained by applying an external voltage bias while measuring the current response with a digital source meter (Keithley 2400). The voltage scan rate was 10 mV s⁻¹ and no device preconditioning, such as light soaking or forward voltage bias applied for long time, was applied before starting the measurement. The starting voltage was determined as the potential at which the cells furnishes 1 mA in forward bias, no equilibration time was used. The cells were masked with a black metal mask (0.16 cm²) to estimate the active area and reduce the influence of the scattered light.

Example 3: Photovoltaic Characterization of Solar Cells of the Invention

Figure 2:
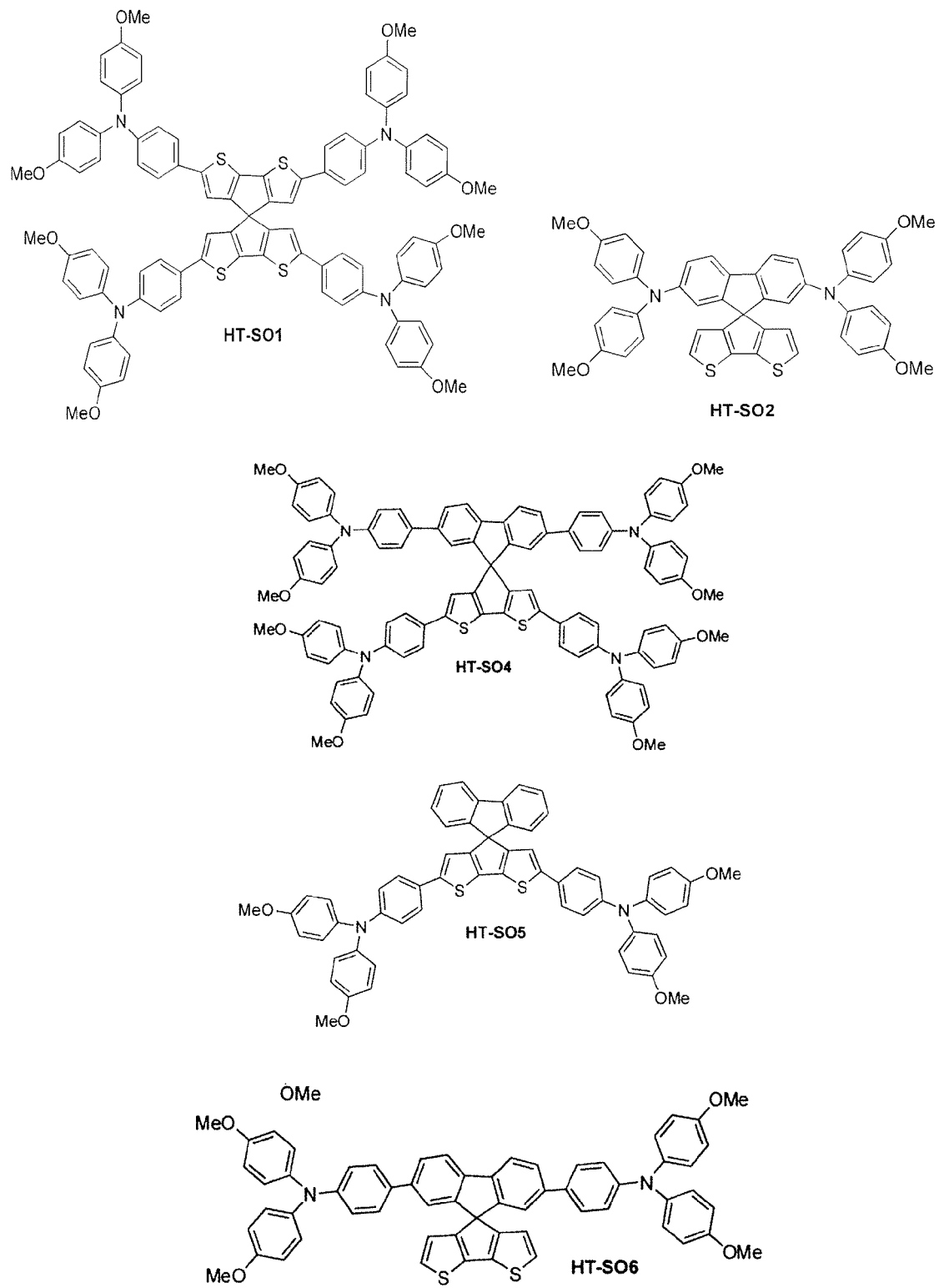
FIG. 2 shows the specific structures of compounds according to the invention being HT-SO2, HT-SO4 and HT-SO6; HT-SO1 and HT-SO5 are shown for the purpose of comparison.

HT-SO2, HT-SO4 and HT-SO6 are compounds according to the invention and described in FIG. 2. HT-SO1 and HT-SO5 based on a spiro dithiophene structure are shown for the purpose of comparison In Table 1, it can be seen that HT-SO1, HT-SO2, HT-SO4, HT-SO5, and HT-SO6 yielded high photoconversion efficiencies (PCE) varying from 1.3% (HT-SO6 for the "standard" perovskite) to 20.2% (HT-SO2 for the "mixed" perovskite). The highest short circuit current densities ($J_{sc}$) were recorded for the HT-SO5 and HT-SO2 with 20.24 mA cm⁻² and 23.4 mA cm⁻² respectively. This is closed to the theoretical Shockley Queisser limit underlying that these HTMs are close or exceeding state-of-the-art HTMs such as Spiro-OMeTAD. Especially HT-SO2 has consistently outcompeted comparable Spiro-OMeTAD control cells in both fill factor (FF) and open circuit voltage ($V_{oc}$). It should be noted that this comparison is done for efficiency values which are among the highest recorded to date. Thus, these HTMs have the potential to replace Spiro altogether due to their more inexpensive synthesis route.

The exact performance parameters can be seen for the best current-voltage (JV) scans for the respective HTMs. The voltage scan rate was 10 mV s$^{-1}$ and no device preconditioning was applied before starting the measurement, such as light soaking or forward voltage bias applied for long time. These conditions are similar to the protocols of solar cell certification. Moreover, the hysteresis was negligibly low (<1.5%). This means the recorded values are representative of what can be realistically expected when operated under operating conditions. It should be noted that the described HTMs are doped with additives: tBP, LiTFSI, and Co, in order to ensure better charge transport dynamics (see Materials and Methods above for the exact compositions). This is typically done for Spiro-OMeTAD as well.

The highest performing HT-SO2 cell (20.2%) was measured after a few days again and still exhibited similar efficiencies indicating good stability when kept in a light-tight desiccator.

TABLE 1

Figure 3A:
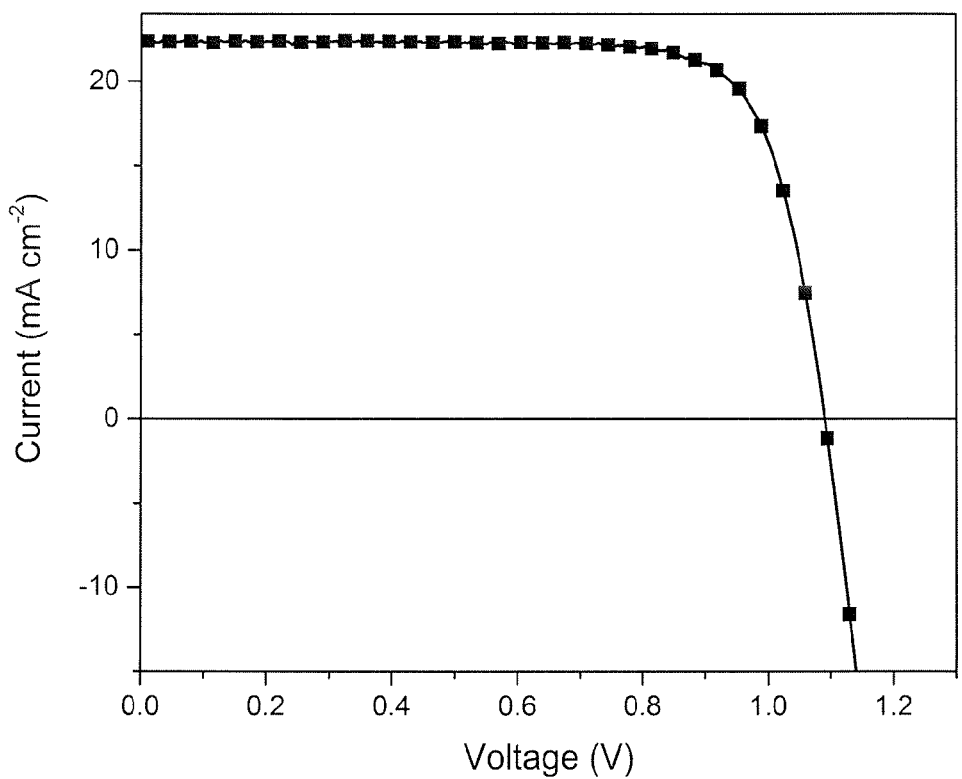
FIGS. 3A, B, C and D show the Current-Voltage curves (forward scans) of solid state solar cells comprising the compounds of the invention: HT-SO2 (FIG. 3A), HT-SO4 (FIG. 3B) and HT-SO6 (FIG. 3D), and "mixed" organic-inorganic perovskite (perovskite with mixed formamidinium methylammonium cations and mixed iodine bromine anions as sensitizer and HT-SO5 (FIG. 3C) and "mixed" organic-inorganic perovskite as sensitizer for comparison.
Figure 3B:
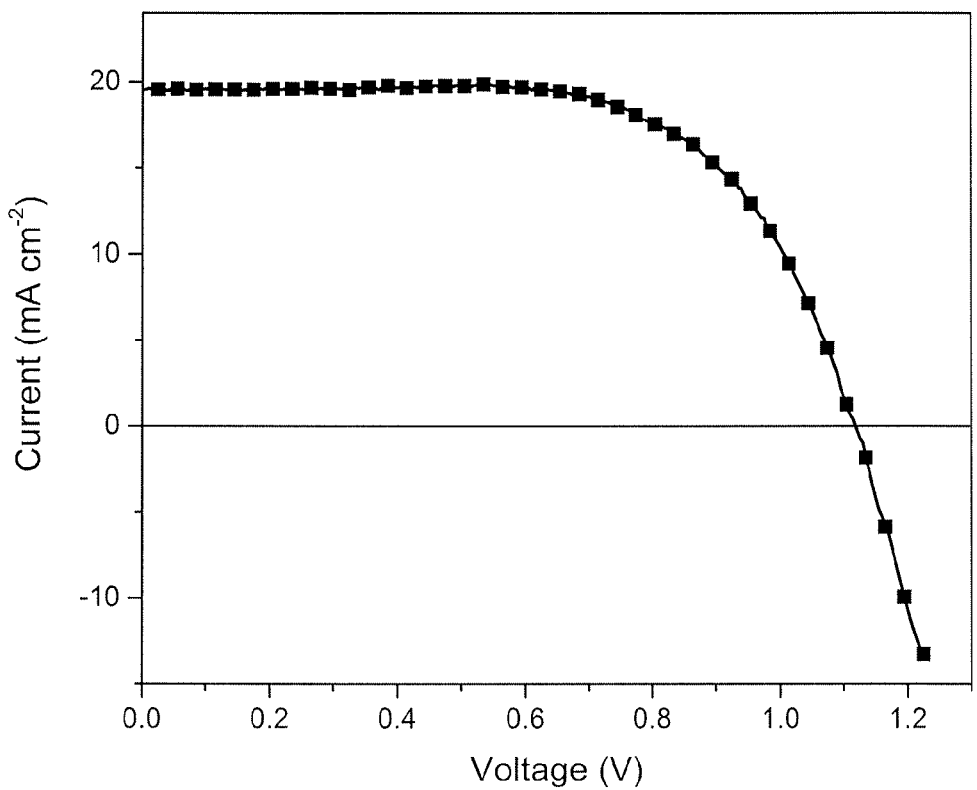
Figure 3C:
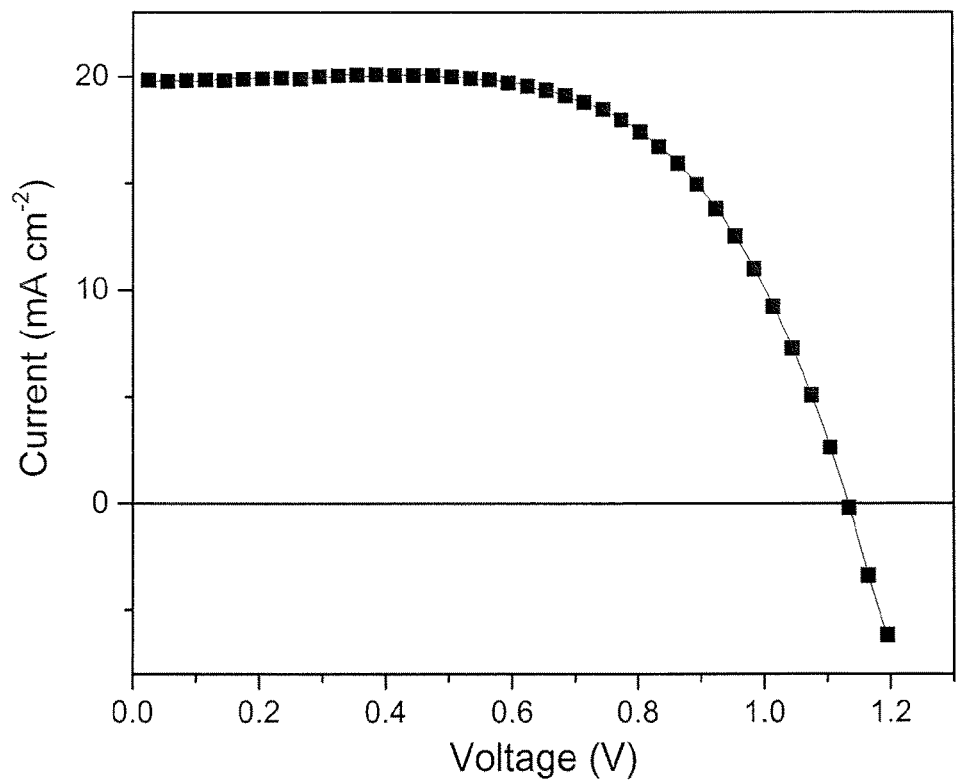
Figure 3D:
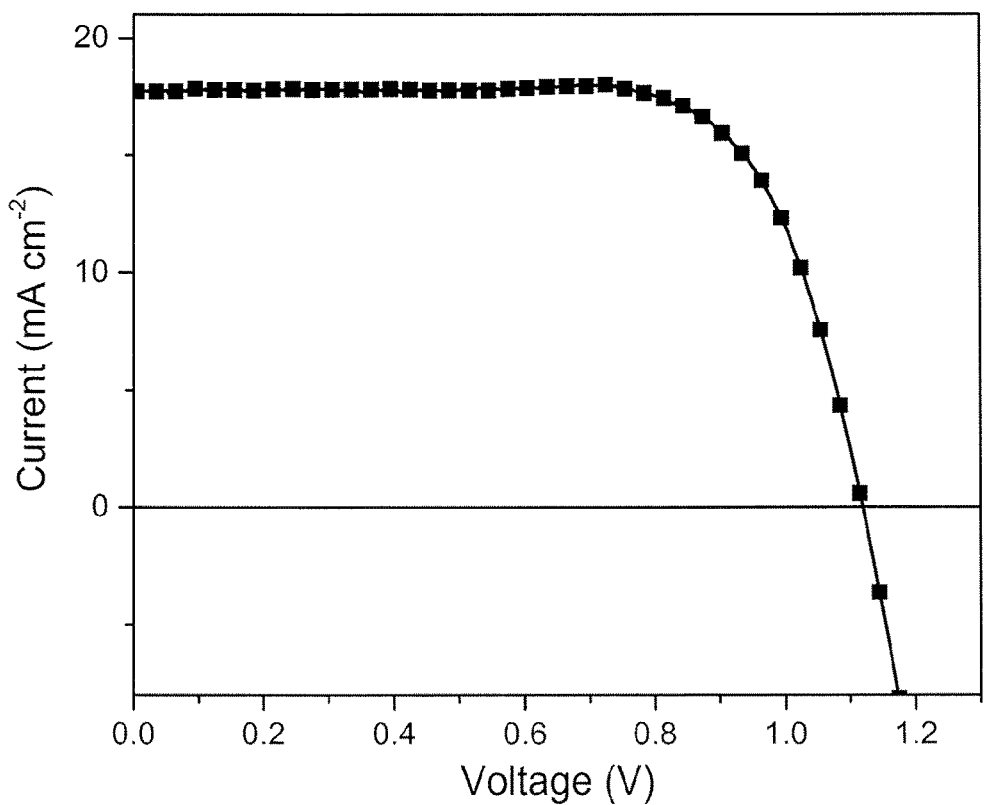

Photovoltaic properties of solar cells comprising a compound of the invention as hole transporting material and "mixed" perovskite (perovskite with mixed formamidinium methylammonium cations and mixed iodine bromine anions) or standard perovskite (perovskite with methylammonium cation) in the sensitizer layer (see FIGS. 3A, 3B, and 3C)

| Compounds | $J_{sc}$ [mAcm$^{-2}$] | $V_{oc}$ [mV] | FF | PCE [%] | Perovskite |
|---|---|---|---|---|---|
| HT-SO1 | 18.4 | 1069 | 0.33 | 6.6 | mixed |
| HT-SO2 | 23.4 | 1091 | 0.78 | 20.2 | mixed |
| HT-SO4 | 19.5 | 1118 | 0.649 | 14.3 | mixed |
| HT-SO5 | 20.2 | 1113 | 0.74 | 16.7 | mixed |
| HT-SO6 | 17.7 | 1119 | 0.734 | 14.6 | mixed |
| HT-SO1 | 17.2 | 988 | 0.73 | 13.4 | standard |
| HT-SO2 | 20.9 | 1100 | 0.76 | 17.7 | standard |
| HT-SO5 | 9.4 | 953 | 0.64 | 5.7 | standard |
| HT-SO4 | 18.8 | 1094 | 049 | 10.2 | standard |
| HT-SO6 | 4.2 | 923 | 0.33 | 1.3 | standard |

The invention claimed is:
1. A compound of formula (I)

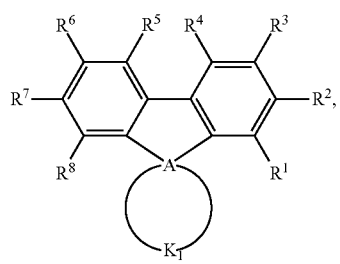

(I)

wherein
   A is selected from Si or C atom;
   $K_1$ is a conjugated system or a system of fused aromatics rings or fused non-aromatic rings comprising at least one heteroatom being selected from O, S and N, wherein said aromatic rings may be further substituted by substituents being independently selected from H, from substituents comprising 1-50 carbons, 1-20 heteroatoms being selected from O, S, N, from halogen being selected from Cl, F, Br, from —C≡N, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(═O)—, wherein alkyl, heteroalkyl, alkylaryl if they comprise 3 or more carbons, may be linear, branched or cyclic, and from substituents being independently selected from a substituent of formula (1);

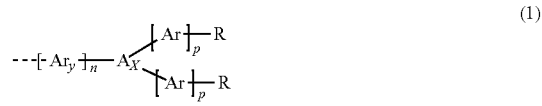

(1)

wherein
   n and p is an integer selected from 0, 1 or 2;
   $A_X$ is selected from N or P(═O);
   $Ar_y$ and Ar are independently selected from a monocyclic system or a polycyclic system comprising fused aromatic rings or conjugated monocyclic aromatic rings, said ring comprising 0, 1 or 2 heteroatoms being selected from O, S and N, and is further substituted in addition to R by other substituents independently selected from H, halogen, C1-C10 alkyl, C1-C10 alkoxy group, C1-C10 alkylthio (—S-alkyl) and —C≡N;
   R is selected from H, $R_1$, —$NR_1R_2$, —O—$R_1$, —P(═O) $R_1R_2$, —S—$R_1$, or halogen, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl, wherein said alkyl, alkoxy, alkoxyalkyl, alkenyl and alkynyl, if they comprise 3 or more carbons, may be linear, branched or cyclic and wherein aryl, heteroaryl, alkyl, alkenyl, alkynyl may be further substituted by alkoxy group, alkylthio group and alkyl;
wherein
   said compound of formula (1) is selected from a compound of formula (Ia), (Ib) or (Ic)

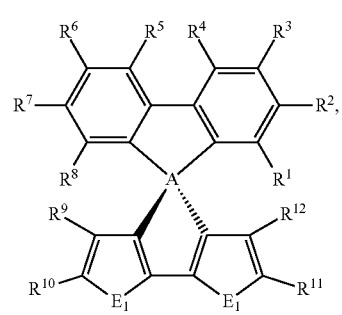

(Ia)

-continued

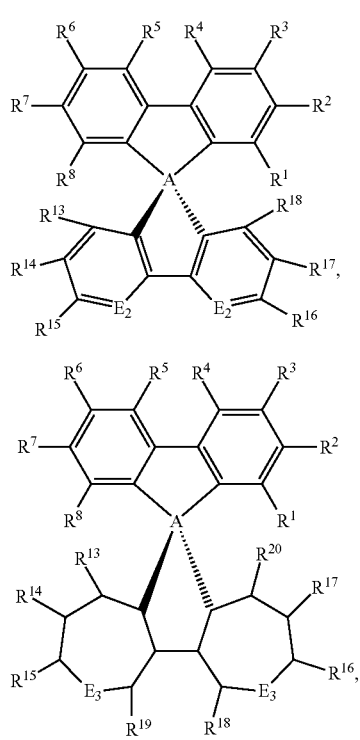

wherein
E₁ is selected from O, S and N, E₂ is selected from OR²² or SR²², R²² being selected from BF₄⁻, PF₆⁻, CF₃SO₃⁻ and halogen⁻ being selected from Cl⁻, F⁻, Br⁻, or I⁻, E₃ is selected from O, S, NR²¹ or N, wherein R²¹ is independently selected from H, halogen being selected from Cl, F, Br, or I, from C1-C30 alkyl, C1-C30 heteroalkyl, C4-C30 aryl and C4-C30 heteroaryl, the heteroatom being selected from O, S, and N;

R⁹, R¹⁰, R¹¹, R¹², R¹³, R¹⁴, R¹⁵, R¹⁶, R¹⁷, R¹⁸, R¹⁹ and R²⁰ are independently selected from H, halogen being selected from Cl, F, Br, or I, from —C≡N, C1-C30 alkyl, C1-C30 heteroalkyl, C4-C20 aryl, C4-C20 heteroaryl, C4-C30 alkylaryl group, C4-C30 aryloxy group or C4-C20 heteroaryloxy group, wherein the heteroatom is selected from O, S, N and —P(=O)—, wherein alkyl, heteroalkyl, alkylaryl if they comprise 3 or more carbons, may be linear, branched or cyclic, and from a substituent being independently selected from a substituent of formula (1); and wherein
R¹, R², R³, R⁴, R⁵, R⁶, R⁷ and R⁸ is independently selected from H, substituents comprising 1-50 carbons, 1-20 heteroatoms being selected from O, S, N, from halogen being selected from Cl, F, Br, from —C≡N, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, and wherein alkyl, heteroalkyl, alkylaryl if they comprise 3 or more carbons, may be linear, branched or cyclic;

at least one R¹, R², R³, R⁴, R⁵, R⁶, R⁷ and R⁸ is different from H; and at least one R¹, R², R³, R⁴, R⁵, R⁶, R⁷ or R⁸ being different from H atom is independently selected from a substituent of formula (1).

2. The compound according to claim 1, wherein Ar_y and Ar are independently selected from moieties according to any one of formulae (2) to (19)

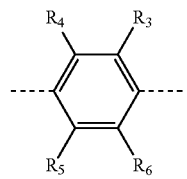

(2)

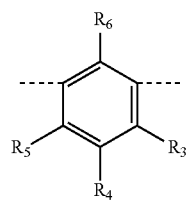

(3)

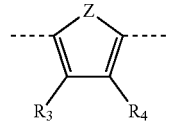

(4)

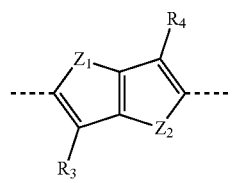

(5)

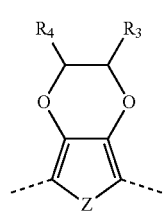

(6)

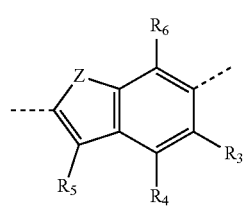

(7)

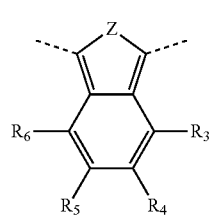

(8)

(9) 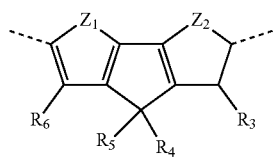

(10) 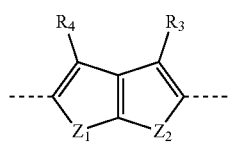

(11) 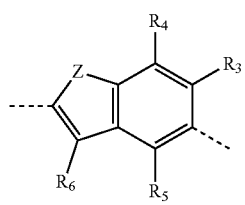

(12) 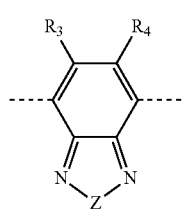

(13) 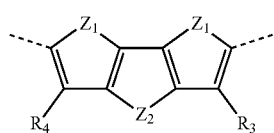

(14) 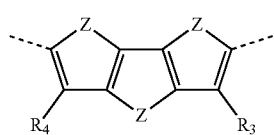

(15) 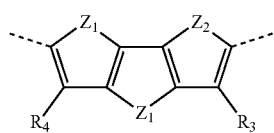

(16) 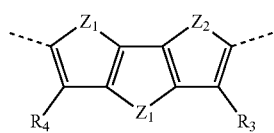

(17) 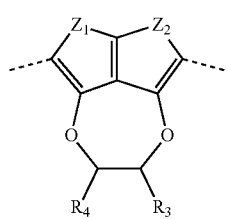

(18) 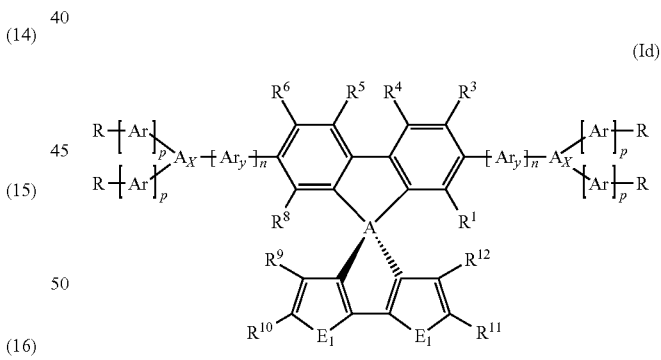

(19) 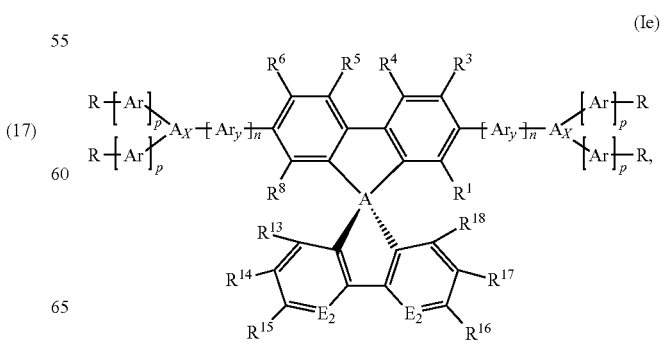

wherein
Z, $Z_1$, $Z_2$ are independently selected from O, S and Se atoms,
$R_3$, $R_4$, $R_5$ and $R_6$ are independently selected from H, halogen, C1-C10 alkyl, C1-C10 alkoxy group, C1-C10 alkylthio (—S-alkyl) and —C≡N.

3. The compound according to claim 1, wherein $R^{10}$ and $R^{11}$ of compound of formula (Ia), and/or $R^{15}$ and $R^{16}$ of a compound according to formula (Ib) or (Ic), or $R^{14}$ and $R^{17}$ of a compound according to formula (Ib) or (Ic) are selected from a substituent of formula (1).

4. The compound according to claim 1, wherein the compound of formula (I) is selected from a compound according to any one of formulae (Id), (Ie) and (If)

(Id)

(Ie)

-continued

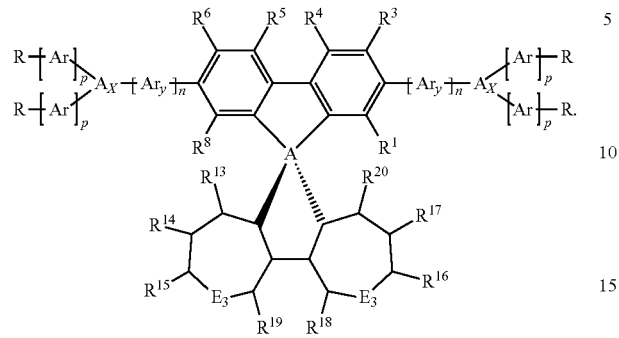

(If)

5. The compound according to claim 1, wherein $R^1$, $R^3$, $R^4$, $R^5$, $R^6$ and $R^8$ is H.

6. The compound according to claim 1, wherein $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are H.

7. A hole transporting material comprising at least one compound selected from a compound according to any one of formulae (Ia), (Ib), and (Ic)

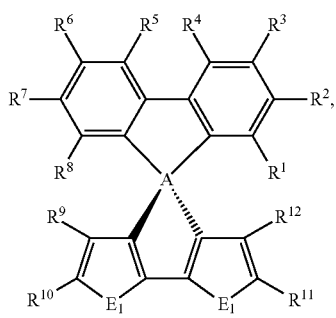

(Ia)

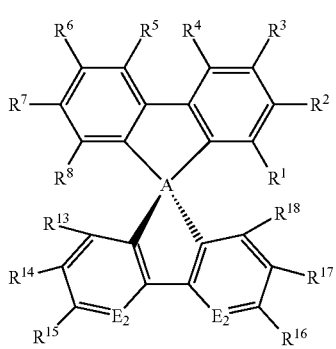

(Ib)

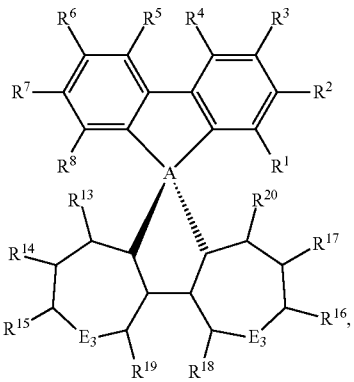

(Ic)

wherein
A is selected from Si or C atom;
$E_1$ is selected from O, S and N, $E_2$ is selected from $OR^{22}$ or $SR^{22}$, $R^{22}$ being selected from $BF_4^-$, $PF_6^-$, $CF_3SO_3^-$ and halogen$^-$ being selected from Cl$^-$, F$^-$, Br$^-$, or I$^-$, $E_3$ is selected from O, S, $NR^{21}$ or N, wherein $R^{21}$ is independently selected from H, halogen being selected from Cl, F, Br, or I, from C1-C30 alkyl, C1-C30 heteroalkyl, C4-C30 aryl and C4-C30 heteroaryl, the heteroatom being selected from O, S, and N;
$R^1$, $R^2$, $R^3$, $R^4$, $R^5$, $R^6$, $R^7$ and $R^8$ is independently selected from H, substituents comprising 1-50 carbons, 1-20 heteroatoms being selected from O, S, N, from halogen being selected from Cl, F, Br, from —C≡N, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(=O)—, and wherein alkyl, heteroalkyl, alkylaryl if they comprise 3 or more carbons, may be linear, branched or cyclic;
at least one $R^1$, $R^2$, $R^3$, $R^4$, $R^5$, $R^6$, $R^7$ and $R^8$ is different from H; and
at least one $R^1$, $R^2$, $R^3$, $R^4$, $R^5$, $R^6$, $R^7$ or $R^8$ being different from H atom is independently selected from a substituent of formula (1);
$R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are independently selected from H, halogen being selected from Cl, F, Br, or I, from —C≡N, C1-C30 alkyl, C1-C30 heteroalkyl, C4-C20 aryl, C4-C20 heteroaryl, C4-C30 alkylaryl group, C4-C30 aryloxy group or C4-C20 heteroaryloxy group, wherein the heteroatom is selected from O, S, N and —P(=O)—, wherein alkyl, heteroalkyl, alkylaryl if they comprise 3 or more carbons, may be linear, branched or cyclic, and from a substituent being independently selected from a substituent of formula (1);

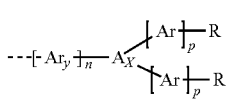

(1)

wherein
n and p is an integer selected from 0, 1 or 2;
$A_X$ is selected from N or P(=O);
$Ar_y$ and Ar are independently selected from a monocyclic system or a polycyclic system comprising fused aromatic rings or conjugated monocyclic aromatic rings, said ring comprising 0, 1 or 2 heteroatoms being selected from O, S and N, and is further substituted in addition to R by other substituents independently selected from H, halogen, C1-C10 alkyl, C1-C10 alkoxy group, C1-C10 alkylthio (—S-alkyl) and —C≡N;

R is selected from H, $R_1$, —$NR_1R_2$, —O—$R_1$, —P(=O) $R_1R_2$, —S—$R_1$, or halogen, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl, wherein said alkyl, alkoxy, alkoxyalkyl, alkenyl and alkynyl, if they comprise 3 or more carbons, may be linear, branched or cyclic and wherein aryl, heteroaryl, alkyl, alkenyl, alkynyl may be further substituted by alkoxy group, alkylthio group and alkyl.

8. Hole transporting material according to claim 7, wherein the at least one compound is selected from a compound according to any one of formulae (Id), (Ie) and (If)

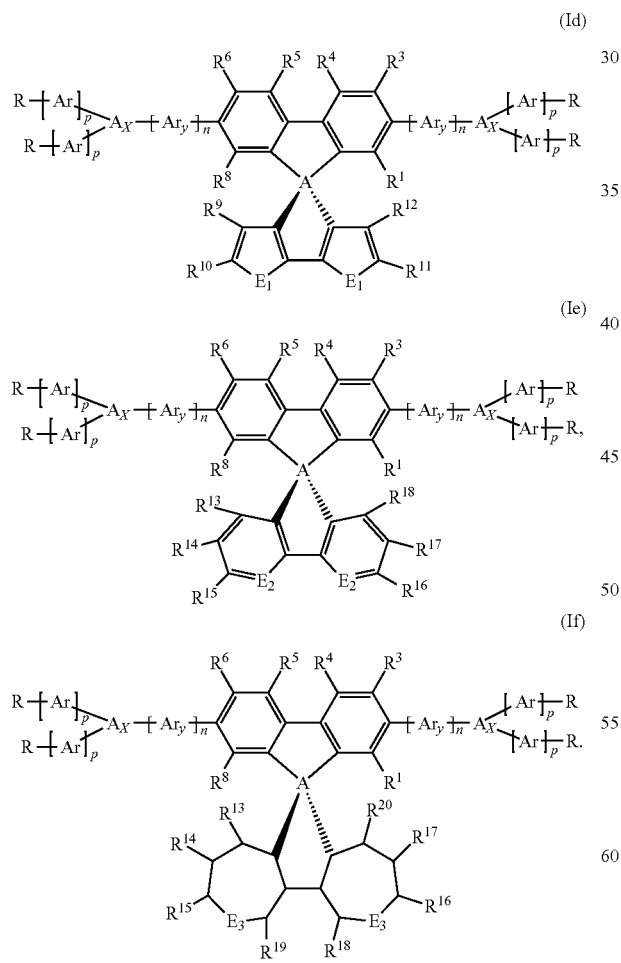

9. An optoelectronic and/or photoelectrochemical device being selected from an organic photovoltaic device, a photovoltaic solid state device, an p-n heterojunction, an organic solar cell, a dye sensitized solar cell, a solid state solar cell, and a phototransistor, and comprising at least one compound selected from a compound according to any one of formulae (Ia), (Ib), and (Ic)

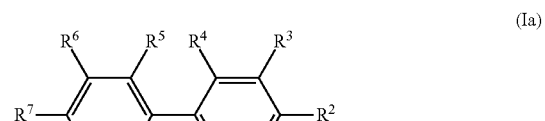

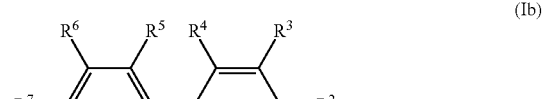

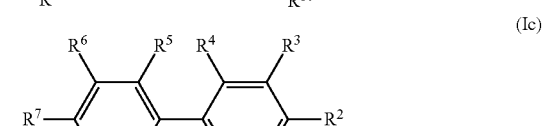

wherein

A is selected from Si or C atom;

$E_1$ is selected from O, S and N, $E_2$ is selected from $OR^{22}$ or $SR^{22}$, $R^{22}$ being selected from $BF_4^-$, $PF_6^-$, $CF_3SO_3^-$ and halogen$^-$ being selected from Cl$^-$, F$^-$, Br$^-$, or I$^-$, $E_3$ is selected from O, S, $NR^{21}$ or N, wherein $R^{21}$ is independently selected from H, halogen being selected from Cl, F, Br, or I, from C1-C30 alkyl, C1-C30 heteroalkyl, C4-C30 aryl and C4-C30 heteroaryl, the heteroatom being selected from O, S, and N;

$R^1$, $R^2$, $R^3$, $R^4$, $R^5$, $R^6$, $R^7$ and $R^8$ is independently selected from H, substituents comprising 1-50 carbons, 1-20 heteroatoms being selected from O, S, N, from halogen being selected from Cl, F, Br, from —C≡N, from C1-C30 alkyl, C1-C30 heteroalkyl, C4-C20 aryl group, C4-C20 heteroaryl group, C4-C30 alkylaryl group, C4-C30 aryloxy group or C4-C20 heteroaryloxy group, wherein the heteroatom is selected from O, S, Se, N and —P(═O)—, and wherein alkyl, heteroalkyl, alkylaryl if they comprise 3 or more carbons, may be linear, branched or cyclic;

at least one $R^1$, $R^2$, $R^3$, $R^4$, $R^5$, $R^6$, $R^7$ and $R^8$ is different from H; and at least one $R^1$, $R^2$, $R^3$, $R^4$, $R^5$, $R^6$, $R^7$ or $R^8$ being different from H atom is independently selected from a substituent of formula (1);

$R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are independently selected from H, halogen being selected from Cl, F, Br, or I, from —C≡N, C1-C30 alkyl, C1-C30 heteroalkyl, C4-C20 aryl, C4-C20 heteroaryl, C4-C30 alkylaryl group, C4-C30 aryloxy group or C4-C20 heteroaryloxy group, wherein the heteroatom is selected from O, S, N and —P(═O)—, wherein alkyl, heteroalkyl, alkylaryl if they comprise 3 or more carbons, may be linear, branched or cyclic, and from a substituent being independently selected from a substituent of formula (1);

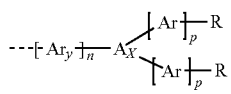

(1)

wherein n and p is an integer selected from 0, 1 or 2;

$A_X$ is selected from N or P(═O);

$Ar_y$ and Ar are independently selected from a monocyclic system or a polycyclic system comprising fused aromatic rings or conjugated monocyclic aromatic rings, said ring comprising 0, 1 or 2 heteroatoms being selected from O, S and N, and is further substituted in addition to R by other substituents independently selected from H, halogen, C1-C10 alkyl, C1-C10 alkoxy group, C1-C10 alkylthio (—S-alkyl) and —C≡N;

R is selected from H, $R_1$, —$NR_1R_2$, —O—$R_1$, —P(═O) $R_1R_2$, —S—$R_1$, or halogen, wherein $R_1$ and $R_2$ are independently selected from C4-C20 aryl, C4-C20 heteroaryl, C4-C20 aryloxy group, C4-C20 heteroaryloxy group, C4-C20 alkoxyaryl, C4-C20 alkoxyheteroaryl, C4-C20 aryl aryloxy group, C4-C20 heteroaryl aryloxy group, C1-C20 alkyl, C1-C20 alkoxy group, C1-C20 alkoxyalkyl, C1-C20 alkylthio, C2-C20 alkenyl and C2-C20 alkynyl, wherein said alkyl, alkoxy, alkoxyalkyl, alkenyl and alkynyl, if they comprise 3 or more carbons, may be linear, branched or cyclic and wherein aryl, heteroaryl, alkyl, alkenyl, alkynyl may be further substituted by alkoxy group, alkylthio group and alkyl.

10. The optoelectronic and/or photoelectrochemical device according to claim 9, wherein the at least one compound is selected from a compound according to any one of formulae (Id), (Ie) and (If)

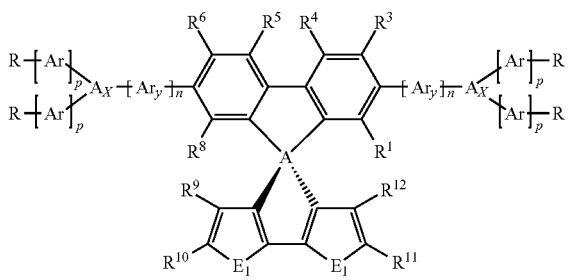

(Id)

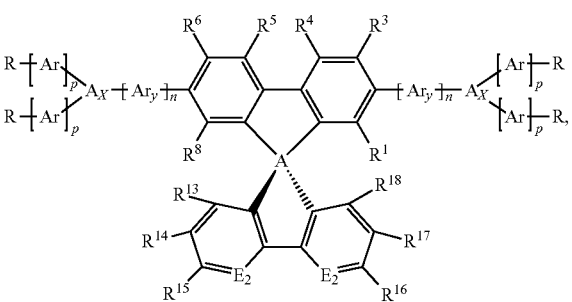

(Ie)

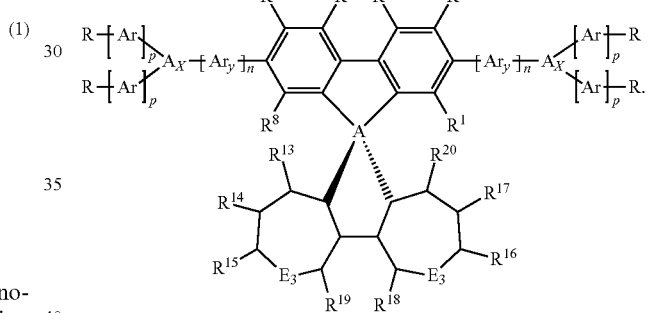

(If)

11. The optoelectronic and/or photoelectrochemical device according to claim 9 comprising a hole transporting layer comprising said at least one compound.

12. The optoelectronic and/or photoelectrochemical device according to claim 9 is selected from a photovoltaic solid state device or a solar cell comprising an organic-inorganic perovskite as sensitizer under the form of a layer.

13. The optoelectronic and/or photoelectrochemical device according to claim 9, wherein the organic-inorganic perovskite layer material comprises a perovskite-structure according any one of formulae (II), (IIa), (IIb), (IIc), (IId) and (IIe) below:

| | |
|---|---|
| WW'MX$_4$ | (II) |
| WMX$_3$ | (IIa) |
| WW'N$_{2/3}$X$_4$ | (IIb) |
| WN$_{2/3}$X$_3$ | (IIc) |
| BN$_{2/3}$X$_4$ | (IId) |
| BMX$_4$ | (IIe), | wherein

W and W' are organic, monovalent cations that are independently selected from primary, secondary, tertiary or quaternary organic ammonium compounds, including N-containing heterorings and ring systems, W and W' having independently from 1 to 60 carbons and 1 to 20 heteroatoms;

B is an organic, bivalent cation selected from primary, secondary, tertiary or quaternary organic ammonium compounds having from 1 to 60 carbons and 2-20 heteroatoms and having two positively charged nitrogen atoms;

M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$;

N is selected from the group of $Bi^{3+}$ and $Sb^{3+}$; and,

X is independently selected from $Cl^-$, $Br^-$, $I^-$, $NCS^-$, $CN^-$, and $NCO^-$.

14. The optoelectronic and/or photoelectrochemical device according to claim 9, wherein the at least one compound is a tuner of HOMO level.

\* \* \* \* \*

UNITED STATES PATENT AND TRADEMARK OFFICE
CERTIFICATE OF CORRECTION

| | | |
|---|---|---|
| PATENT NO. | : 10,727,414 B2 | Page 1 of 1 |
| APPLICATION NO. | : 15/738279 | |
| DATED | : July 28, 2020 | |
| INVENTOR(S) | : Michael Saliba et al. | |

It is certified that error appears in the above-identified patent and that said Letters Patent is hereby corrected as shown below:

In the Specification

Column 3
- Line 26: "... P(=O)-, from and wherein alkyl, ..." to be replaced with "... P(=O)-, from -C≡N, and wherein alkyl, ..."

Column 9
- Line 55: "... selected from $OR^2$ ..." to be replaced with "... selected from $OR^{22}$ ..."

Column 26
- Line 7: "... HT-SO07 ..." to be replaced with "... HT-SO7 ..."
- Line 8: "... HT-SO09 ..." to be replaced with "... HT-SO9 ..."
- Line 58: "... HT-SO02 ..." to be replaced with "... HT-SO2 ..."

Column 28
- Line 36: "... The residue was taken up in $CH_2C2$ ..." to be replaced with "... The residue was taken up in $CH_2Cl_2$ ..."
- Line 49: "... $NH_2NH_2H_2O$ ..." to be replaced with "... $NH_2NH_2 \cdot H_2O$ ..."

Column 30
- Lines 18-19: "... [2,1-:3,4- b'] ..." to be replaced with "... [2,1-b-:3,4-b'] ..."
- Line 46: "... (400 MHz, $CDCl_3$+1% v/v $NH_2NH_2$-$H_2O$): ..." to be replaced with "... (400 MHz, $CDCl_3$ + 1% v/v $NH_2NH_2 \cdot H_2O$): ..."
- Lines 52-53: "... (100.6 MHz, $CDCl_3$+1% v/v $NH_2NH_2$-$H_2O$): ..." to be replaced with "... (100.6 MHz, $CDCl_3$ + 1% v/v $NH_2NH_2 \cdot H_2O$): ..."

Column 32
- Line 33: "... (Priizisions Glas & Optik ..." to be replaced with "... (Präzisions Glas & Optik ..."

Signed and Sealed this
Twenty-second Day of September, 2020

Andrei Iancu
*Director of the United States Patent and Trademark Office*